US008287821B2

(12) United States Patent
Nakahana et al.

(10) Patent No.: US 8,287,821 B2
(45) Date of Patent: Oct. 16, 2012

(54) SAMPLE STORAGE

(76) Inventors: Yoko Nakahana, Hyogo (JP);
Shinichiro Kakuda, Hyogo (JP)

( * ) Notice: Subject to any disclaimer, the term of this patent is extended or adjusted under 35 U.S.C. 154(b) by 110 days.

(21) Appl. No.: 12/934,250

(22) PCT Filed: Mar. 11, 2009

(86) PCT No.: PCT/JP2009/055223
§ 371 (c)(1),
(2), (4) Date: Dec. 10, 2010

(87) PCT Pub. No.: WO2009/150881
PCT Pub. Date: Dec. 17, 2009

(65) Prior Publication Data
US 2011/0085951 A1    Apr. 14, 2011

(30) Foreign Application Priority Data
Jun. 10, 2008    (JP) .................................. 2008-152249

(51) Int. Cl.
*B01L 3/14*            (2006.01)
(52) U.S. Cl. ..... 422/550; 422/568; 422/931; 435/288.1; 435/304.1; 215/6; 356/246
(58) Field of Classification Search .................. 422/550, 422/568, 931; 435/288.1, 304.1; 215/6; 356/246
See application file for complete search history.

(56) References Cited

U.S. PATENT DOCUMENTS

| 4,007,639 | A |   | 2/1977  | Haeckel |            |
|-----------|---|---|---------|---------|------------|
| 4,140,489 | A | * | 2/1979  | Lee     | 435/39     |
| 5,882,601 | A | * | 3/1999  | Kath et al. | 422/570 |
| 6,066,299 | A | * | 5/2000  | Lodge   | 422/547    |
| 6,270,728 | B1|   | 8/2001  | Wijnschenk et al. |  |
| 6,821,785 | B1| * | 11/2004 | Anraku et al. | 436/66 |
| 8,104,611 | B2| * | 1/2012  | Helou, Jr. | 206/219 |

FOREIGN PATENT DOCUMENTS

| EP | 0 295 047    | 12/1988 |
|----|--------------|---------|
| JP | 61-033657 A  | 2/1986  |
| JP | 1987-37743 U | 3/1987  |
| JP | 9-507037 A   | 7/1997  |
| JP | 3043865 U    | 9/1997  |
| JP | 11-174060 A  | 7/1999  |

(Continued)

*Primary Examiner* — In Suk Bullock
*Assistant Examiner* — Timothy G Kingan
(74) *Attorney, Agent, or Firm* — Hamre, Schumann, Mueller & Larson, P.C.

(57)    ABSTRACT

A sample storage, in which barcodes and two-dimensional codes written on the outer surface of the sample storage can be read correctly without false recognition. A storage tube 110 is made of transparent material, comprising a top opening. An externally equipped opaque writable element 120 is assembled outside by covering storage tube 110 throughout from the bottom surface to the side surface. An externally equipped opaque writable element 120 is to be used as a medium to which coded information that can be read by means of optical reading is written. The top opening of the storage container 110 is sealed by the lid element screwed into or fitted into the externally equipped opaque writable element 120 not to the storage container 110. At least one window 125 is provided, which enables a sample 200 contained to be observed, with the externally equipped opaque writable element 120 assembled outside. The horizontal friction generated in the lid element screwing process is blocked and the vertical pressing force is transmitted efficiently by the slide plate 140.

15 Claims, 23 Drawing Sheets

FOREIGN PATENT DOCUMENTS

| | | |
|---|---|---|
| JP | 2001-502595 A | 2/2001 |
| JP | 2002-225895 A | 8/2002 |
| JP | 2005-172682 A | 6/2005 |
| JP | 2009-047597 A | 3/2009 |
| WO | WO95/17253 | 6/1995 |
| WO | WO98/05427 | 2/1998 |

* cited by examiner (a)

(a)

(b)

Top view of the
storage tube 110

(c)

Top view of the
externally equipped
opaque writable
element 120
(color is omitted)

(d)

Bottom view of the
lid element 130
(color is omitted)

(a) [A-A cross sectional view]

(b) [Effect of the slide plate 150]

(a) [Cross sectional view of the conventional storage tube]

(b) [Effect of the conventional gasket when the conventional lid element is rotated]

(a) [A-A cross sectional view]

(b) [Effect of the friction reduction structure 132b]

(a) [A-A cross sectional view]

(b) [Effect of the slide plate 150c]

(a) [A-A cross sectional view]

(b) [Effect of the gasket 140d]

(a) [There is deformation on the edge 12]    [There is a prickle on the edge 12]

(b)

[Gasket is hurt or broken by the prickle on the edge 12

SAMPLE STORAGE

TECHNICAL FIELD

This invention relates to a sample storage that is used for storing a large number of samples, and is applicable to various uses in storing samples. For example, it is used in enclosing and storing developing medicine samples. Also, it is used in storing samples that hold gene information of DNA in the field of medicine.

BACKGROUND ART

In the research and development of medicine and chemistry, storage tubes are used extensively in storing a large number of samples. For example, scientists prepare a large number of samples for a comparative experiment on slightly changing conditions such as blending rate, and they use storage tubes in storing the samples for a required period of time while handling them.

In order to control and store a large number of storage tubes at a time as described above, it is necessary to identify each storage tube. In the past they were identified by handwriting a sample name or identification number directly to the outer surface of storage tubes; however, in recent years sample storages that are controlled by printing a barcode or two-dimensional code on the side and/or bottom surface of the storage tube are highlighted, in which various data and/or control information of a sample are encoded, and then the barcode or two-dimensional code is read in a control process.

A sample storage in the prior art where a barcode or two-dimensional code is written on the side and/or bottom surface thereof is shown below. For example, a sample storage comprises a tubular container 10 that stores samples, and a lid element 20 that directly covers the top opening thereof as shown in FIG. 22 (*a*) or FIG. 22 (*b*).

Container 10 is a tube that stores samples, which forms such a shape similar to a so-called test tube. Simple shaped storage tubes are used in many cases, since mounting a certain structure to container 10 may drive up the costs. In this example, it is made of glass.

Lid element 20 is to cover the top opening of container 10, while for example lid element 20 shown in FIG. 22 (*a*) is a lid made of rubber or a plastic plug. The top opening of container 10 is plugged tightly, and then the top opening of container 10 is closed completely, by pushing lid element 20 into container 10.

Lid element 20 shown in FIG. 22 (*b*) is mounted to container 10 by screwing. The top opening of container 10 is plugged tightly, and the top opening of container 10 is closed completely, by turning and screwing lid element 20. A gasket 30 may be provided on the back of lid element 20.

DISCLOSURE OF THE INVENTION

The Problems to be Solved

The above sample storages of prior art can be controlled by writing a barcode or two-dimensional code directly on the side and/or bottom surface thereof using ink, etc., and then reading the barcode and/or two-dimensional code.

However, the above sample storages of the prior art have a need to be improved as follows. The first problem is that there is a risk of false recognition due to superimposing of a barcode or two-dimensional code on the outer surface of the sample storage and a sample contained in the sample storage. The possibility of false recognition due to superimpose on a sample contained in the sample storage may increase, especially when a bar code is indicated large on the side surface. Since the typical use of sample storages is in handling the sample contained, container 10 is made of transparent material so that the condition of the sample contained can be checked visually. While black bars or dots are to be plotted on the surface of transparent container 10 when barcodes or two-dimensional codes are written directly on the outer surface of container 10, reading the barcodes or two-dimensional codes in such a condition may cause false recognition by the recognition systems, such as a scanner, because such black bars or dots plotted on the surface of container 10 are superimposed on the sample contained. Especially when the sample is not transparent liquid, and the color tone of the sample is deep or turbid, the possibility of false recognition by the recognition systems, such as a scanner, may increase. When humans visually check such codes, it may be difficult to read numbers and/or symbols.

Accordingly, both requirements that visual observation of the sample contained should not be obstructed, and that the color tone and turbidity of the sample contained should not affect in reading barcodes or two-dimensional codes on the outer surface have to be satisfied together; however, conventional sample storages do not satisfy two such contradictory requirements.

The second problem is that the crack on the edge of the opening of the container will be generated by the friction between the container 10 and the lid element 20.

The motion of each element during installing the lid element 20 to the container 10 is as follows.

When the lid element 20 is screwed into the container 10, the lid element 20 is rotated horizontally and pressed vertically, the back surface of the lid element 20 is also rotated horizontally and pressed vertically to the top opening of the container 10. If there is the gasket 30 in the back surface of the lid element 20, the gasket 30 is also rotated horizontally and pressed vertically to the top opening of the container 10. Hereinafter, the configuration including the gasket 30 is explained.

The rotary force of the lid element 20 is transmitted to the top opening of the container 10, the gasket 30 is rotated by being pressed to the top opening of the container 10.

If the container 10 is made of glass material, the method for the glass tube processing is done by the hand-made work, the edge of the top opening is not always made as the flat shape, in some cases, deformation, dimples and prickles are generated on the edge of the top opening as shown in FIG. 23(*a*).

If there are prickles on the edge of the top opening and the gasket 30 is rotated by being pressed to the top opening of the container 10, the gasket 30 faced to the deformation and prickles on the edge of the top opening may be cut and deteriorated as shown in FIG. 23 (*b*). If the gasket 30 is broken and deteriorated, the airtightness of the top opening of the container 10 is lost, the test samples are exposed to the outside atmosphere.

If the deformation, dimples and prickles on the edge of the top opening are broken by the rotation friction between the gasket 30 and the fragments are dropped into the samples stored in container 10. The crack and the crevasse will be generated in the portion where the obstacle is broken, the airtightness of the top opening of the container 10 is lost, and the test samples are exposed to the outside atmosphere.

In view of the first problem, the present invention aims at solving the problem of interrupting the watching of inner samples, and solving the problem of having influence of sample condition such as the tone of color and the muddiness when reading the bar code or the two-dimensional code printed on the external-surface, and providing the sample storage from which can be read the bar code and the two-dimensional code printed on the outer surface of the sample storage without the false recognition.

In view of the second problem, the present invention aims at providing the sample storage to transmit only the vertical pressing force to the gasket, not to transmit the horizontal rotary force to the gasket in order to press the gasket to the top opening of the container without the rotation, though the vertical pressing force and the horizontal rotary force are generated simultaneously on the lid element when the lid element is screwed into the externally equipped opaque writable element.

Means of Solving the Problems

To achieve the above first purpose, a sample storage according to the present invention, comprises;

a storage tube having a top opening, which is made of light-transmissive material to enable a contained sample to be observed, an externally equipped opaque writable element used as a medium to which coded information that can be read by means of optical reading already has been written directly, which is assembled outside by covering said storage tube throughout from the bottom surface to the side surface;

a lid element covering the top opening of the storage tube, the lid element can be screwed with or combined with the externally equipped opaque writable element, and at least one window on said externally equipped opaque writable element, provided in the area other than the write area where said coded information is written, which enables said sample contained to be observed.

The storage tube is installed by the externally equipped opaque writable element and the lid element, and which enables said coded information written to said externally equipped opaque writable element to be read, and said sample contained to be observed through said window.

The coded information is written to the coded information write areas that correspond to only the bottom surface, to only the side surface, or to both the bottom surface and the side surfaces of said storage tube.

It is preferable that the externally equipped opaque writable element is made of opaque plastic material to disable said storage tube to be viewed through said coded information write area, so that the color tone and turbidity of said sample contained in said storage tube do not affect reading of the coded information by means of said optical reading.

According to the above-mentioned configuration, the sample stored in the storage tube can be observed through the window, and the medium to which the barcodes and two-dimensional codes are to be written is made of opaque plastic material, the barcodes and two-dimensional codes are not superimposed on the sample, so that the color tone and turbidity of said sample contained in said storage tube do not affect reading of the coded information by means of said optical reading.

There are two methods for writing the coded information to the externally equipped opaque writable element corresponding to the color of the barcodes or two-dimensional codes and the color of the material of the externally equipped opaque writable element.

The first writing method is that the material color of said externally equipped opaque writable element is the same as the color to be expressed as bars or dots of said coded information, and said coded information directly written to said externally equipped opaque writable element is expressed by changing the color of the area other than bars or dots of said coded information to a different color from said material color.

The second writing method is that the material color of said externally equipped opaque writable element is different from the color to be expressed as bars or dots of said coded information, and said coded information directly written to said externally equipped opaque writable element is expressed by changing the color of the area of bars or dots of said coded information to the color to be expressed as bars or dots of said coded information.

In general, barcodes or two-dimensional codes are expressed by the contrast of two colors. When black and white are used, the contrast become highest. The externally equipped opaque writable element is black, the coded information write area can be changed from black to white. When the color of the area where the bars or dots are written is black and the color of the base field is white, the area other than the bars or dots to be written is changed from black to white. On the contrary, when the color of the area where the bars or dots are written is white and the color of the base field is black, the area for the bars or dots to be written is changed from black to white.

Next, to achieve the above second purpose, a sample storage according to the present invention, in addition to the first configuration, further comprises;

a gasket for facing directly to the top opening of said storage container;

a slide plate installed between the inner surface of said lid element and said gasket for blocking the transmission of the horizontal rotary force of said lid element to said gasket;

wherein the slide plate controls so that only the vertical pressing force is transmitted to the gasket, but the horizontal rotary force is not transmitted to the gasket though the vertical pressing force and the horizontal rotary force are generated simultaneously on the inner surface of the lid element when the lid element is screwed into or fitted into the externally equipped opaque writable element.

There are plural methods for controlling the horizontal rotary force and the vertical pressing force.

The first method is that said slide plate comprises a friction reduction structure on the surface facing the inner surface of the lid element for reducing the horizontal friction between the slide plate and the inner surface of the lid element, and the transmission of the horizontal rotary force generated by the lid element to the slide plate is blocked by the friction reduction structure.

The second method is that the lid element comprises a friction reduction structure on the inner surface for reducing the horizontal friction between the slide plate and the inner surface of the lid element, and the transmission of the horizontal rotary force generated by the lid element to the slide plate is blocked by the friction reduction structure.

The third method is that the gasket instead of above-mentioned slide plate comprises a friction reduction structure on the surface facing the inner surface of the lid element for reducing the horizontal friction between the gasket and the inner surface of the lid element, and the transmission of the horizontal rotary force generated by the lid element to the gasket is blocked by the friction reduction structure, so only the pressing force generated by the lid element is transmitted to the gasket.

For example, the friction reduction structure is plural of small prickles. The contacting area to the facing surface becomes small, so the horizontal friction becomes small.

Next, a sample storage according to the present invention can be provided as the coded information is not written and the externally equipped opaque writable element is blank status. A sample storage, comprises;

a storage tube having a top opening, which is made of light-transmissive material to enable a sample contained to be observed, an externally equipped opaque writable element used as a medium to which coded information that can be read by means of optical reading has already been directly written, which is assembled outside by covering said storage tube throughout from the bottom surface to the side surface, a lid element covering the top opening of the storage tube, the lid element can be screwed with or combined with the externally equipped opaque writable element, and at least one window on said externally equipped opaque writable element, provided in the area other than the write area where said coded information is written, which enables said sample contained to be observed; the storage tube being installed by the externally equipped opaque writable element and the lid element, and which enables said coded information written to said externally equipped opaque writable element to be read, and said sample contained to be observed through said window.

Effect of the Invention

A sample storage according to the present invention enables barcodes or two-dimensional codes on the outer surface thereof to be written directly to an externally equipped opaque writable element, and the barcodes or two-dimensional codes to be read correctly without false recognition because the externally equipped opaque writable element is not imposed on a sample contained, since the barcodes or two-dimensional codes are written to an opaque write medium.

A sample storage according to the present invention enables control so that only the vertical pressing force is transmitted to the gasket, but the horizontal rotary force is not transmitted to the gasket though the vertical pressing force and the horizontal rotary force are generated simultaneously on the inner surface of the lid element when the lid element is screwed into or fitted into the externally equipped opaque writable element. The gasket is not hurt or damaged by the horizontal rotary force, and the prickles on the top opening of the storage tube do not break off.

DETAILED DESCRIPTION OF THE PREFERRED EMBODIMENT

Some embodiments of a sample storage according to the present invention are described below in reference to the relevant drawing. Needless to add, the claims of the present invention include but are not limited to the application, configuration, or quantity shown in the following embodiments.

Embodiment 1

A sample storage 100 in embodiment 1 according to the present invention is described.

Figure 1:
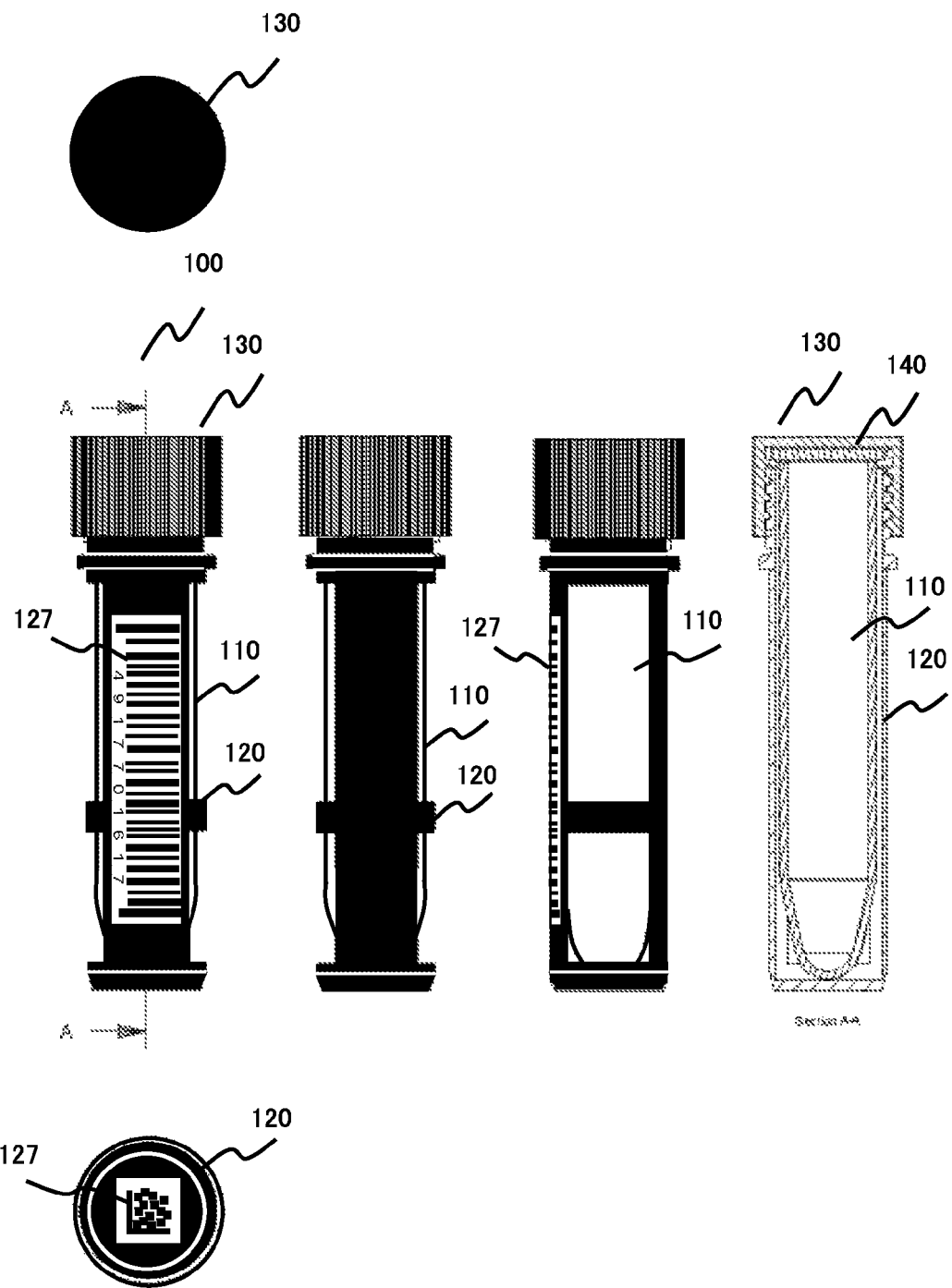
FIG. 1 is a schematic view of the first sample storage 100 in embodiment 1.
Figure 2:
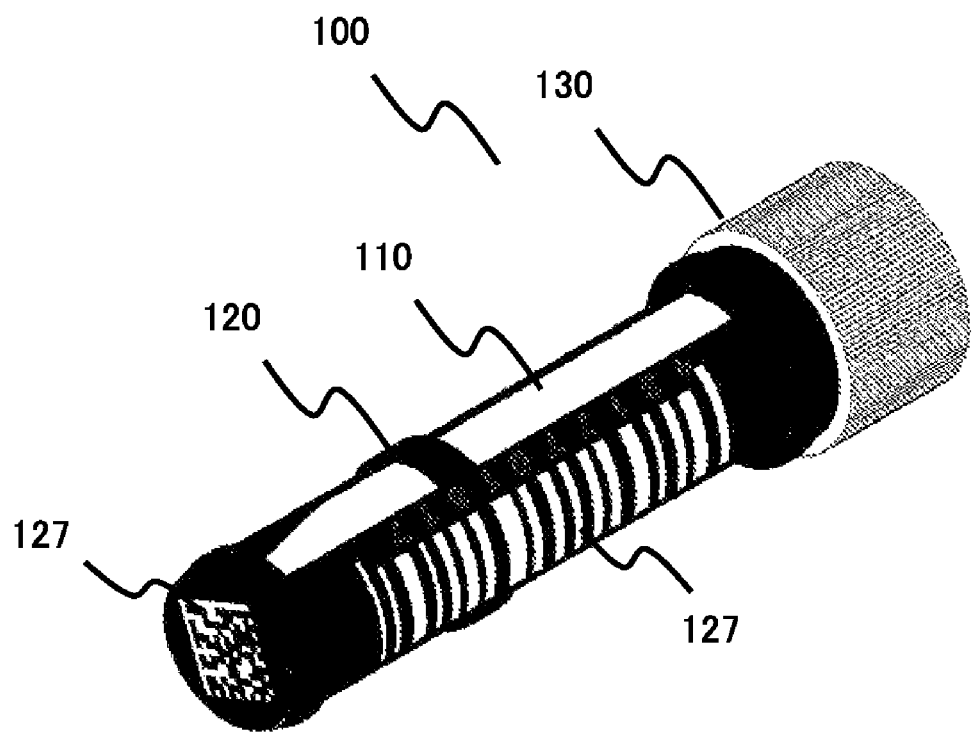
FIG. 2 is a perspective view of the first sample storage 100 in embodiment 1.

FIG. 1 is a schematic view of a sample storage 100 in embodiment 1 according to the present invention. A front view, right side view, back view, top view, bottom view, and A-A cross-sectional view are shown. FIG. 2 is a perspective view, and FIG. 3 is an exploded view of a sample storage 100, which explodes into individual components.

Figure 3:
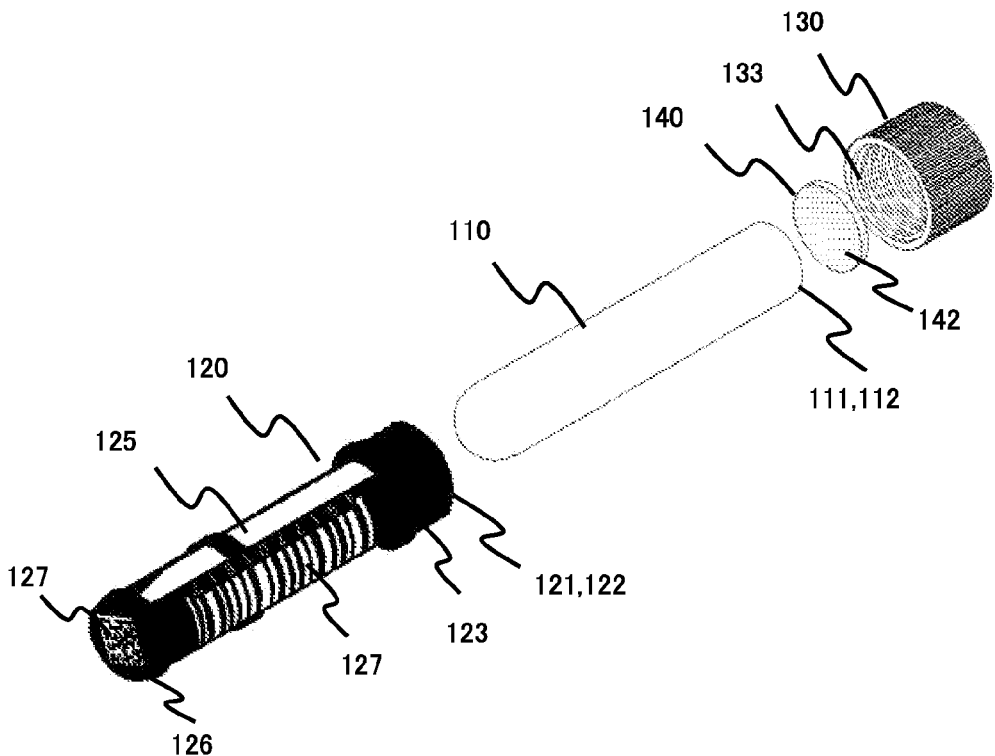
FIG. 3 is an exploded view of the first sample storage 100, which explodes into individual components.
Figure 3:
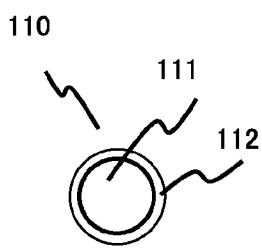
Figure 3:
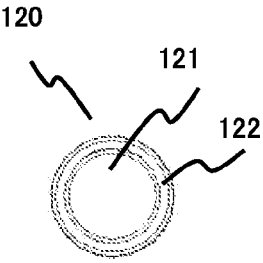
Figure 3:
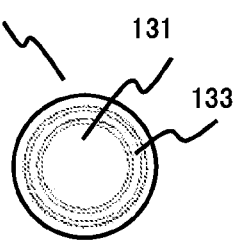

As shown in FIG. 1 through FIG. 3, a sample storage 100 in embodiment 1 comprises a storage tube 110, an externally equipped opaque writable element 120, a lid element 130, and a gasket 140.

While the material color of externally equipped opaque writable element 120 is black as shown in FIG. 1, but in some other figures, the black painting of the externally equipped opaque writable element 120 is omitted for the purpose of better visualization and explanation of other configuration. In addition, the coded information 127, one-dimensional barcodes or two-dimensional dot codes, comprises black bars or black dots, but in some figures, just outline of the bars or dots without black painting is drawn for the purpose of better visualization and explanation of other configuration.

Storage tube 110 is a tubular container having a top opening 111 on the top surface, which stores samples. A top edge 112 of the top opening forms a flat surface, which faces a bottom surface 142 of gasket 140 as described hereinbelow. In this embodiment, storage tube 110 has a tubular shape; however, it may take other forms according to its intended use, etc. Storage tube 110 is made of transparent or translucent light-transmissive material. Any material that is suitable for sample storage and that enables the sample contained to be observed is applicable, including plastic such as polypropylene, and glass. When translucent material is used in order to reduce the effect of ultraviolet rays, etc., any material that enables the sample contained to be observed is applicable, even if it is colored white or brown.

Externally equipped opaque writable element 120 is assembled so as to cover the storage tube 110 throughout from the bottom surface to the side surface, which is used as a medium in which coded information can be written directly, and is assembled to the outside of the storage tube 110. In this embodiment, its original color is black, but the original black color can be changed to white by method described hereinafter. In some figures, the black coloring is omitted for the purpose of better visualization and explanation.

The inner wall of externally equipped opaque writable element 120 forms a tubular shape, so that the inner wall of externally equipped opaque writable element 120 just fits to the outer shape of the storage tube 110. It is assembled outside directly to the storage tube 110 by fitting without adhesive agent.

The outer wall of externally equipped opaque writable element 120 does not necessarily form such a test tube shape as storage tube 110, it may take various shapes.

There is a top opening 121 on the top of the externally equipped opaque writable element 120. The storage tube 110 is inserted to the externally equipped opaque writable element 120 through the top opening 121. A top edge 122 of the opening of externally equipped opaque writable element 120 forms a flat surface.

A thread 123 is formed on the outer wall on the top of the externally equipped opaque writable element 120. In this embodiment, the thread 123 is a male screw. The thread 123 is screwed together with the thread 133 formed on the inner wall of lid element 130 as described hereinbelow.

The side surface of the externally equipped opaque writable element 120 forms a side surface writable area 124, which is used as a space to write coded information, such as barcodes and two-dimensional codes. While any area can be a write area because the color of the externally equipped opaque writable element 120 can be changed its color from black of the original base color to white as described below, a limited part of the side surface is used as a side surface writable area 124 in this embodiment. Thus, once identification information is provided to the side surface writable area 124 on the side surface by printing barcodes or two-dimensional codes, the identification information of the sample storage 100 can be read by non-contact scanning of the side surface writable area 124 from the side of the sample storage 100.

A window 125 is formed in the area other than the side surface writable area 124 on the side surface of the externally equipped opaque writable element 120, so that the storage tube 110 can be observed from the outside. Conditions of the stored sample can be observed easily from the outside through the window 125.

In this embodiment, a flat disc shaped bottom surface writable area 126 is formed at the bottom end of the externally equipped opaque writable element 120. This bottom section acts to allow the sample storage 100 stand by itself, and to form the bottom surface writable area 126, which is used as a medium to which the code such as the two-dimensional codes can be printed. As described above, the externally equipped opaque writable element 120 is assembled outside throughout from the bottom surface to the side surface, and the bottom surface writable area 126 forms an area that is used as a medium to which the code such as the two-dimensional codes are printed. Thus, once identification information is provided to the bottom surface writable area 126 by printing the two-dimensional codes, the identification information of the sample storage 100 can be read by non-contact scanning of the bottom surface writable area 126 from the bottom of the sample storage 100.

Figure 4:
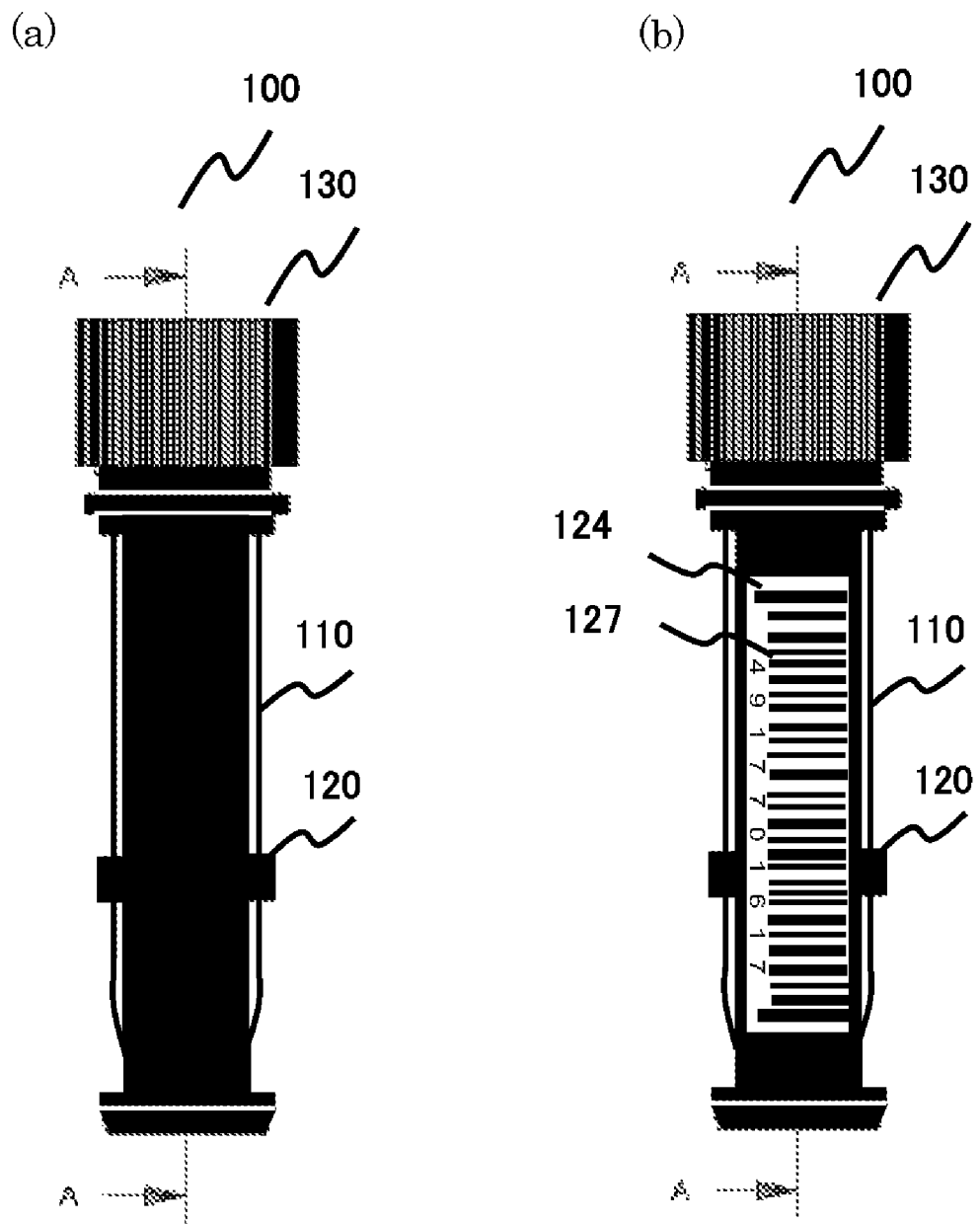
FIG. 4 is a schematic view of an embodiment showing how to write coded information to an externally equipped opaque writable element 120.

FIG. 4 shows an embodiment of how to write coded information to the externally equipped opaque writable element 120. FIG. 4 (*a*) shows the externally equipped opaque writable element 120 before writing the coded information. Its original color is black. It is a feature that the black base of the externally equipped opaque writable element 120 is the same color as of bars or dots that comprise barcodes or two-dimensional codes. The surface of the externally equipped opaque writable element 120 is coated with the resin whose color is changed physically to white by heating in this embodiment.

FIG. 4 (*b*) shows that the color changing of the area other than bars or dots, that area turns to be the base area where the bar code of dot code are described, is changed to white from black using a thermal head. In this embodiment, a barcode is formed. Thus, coded information can be written directly to the externally equipped opaque writable element 120, by changing the color of the base area other than bars or dots portion, but without writing bars or dots with black ink.

In this embodiment, coded information is formed to both the side surface writable area 124 on the side surface, and the bottom surface writable area 126.

While the lid element 130 is to plug a top opening 111 of the storage tube 110, the top opening 121 on the top of the externally equipped opaque writable element 120 is closed by the inner back side 131 of the lid element 130 in this embodiment.

In this embodiment, the thread 133 is formed on the inner wall surface of the lid element 130, which is screwed together with the thread 123 on the externally equipped opaque writable element 120; however, other configurations are possible. For example, the thread 123 is formed on the storage tube 110, but not on the externally equipped opaque writable element 120, the thread 133 on the lid element 130 is screwed together with the thread 123 on the storage tube 100. In addition, as described above, the thread 123 on the storage tube 110 may be a male screw, and thread 133 on lid element 130 may be a female screw; on the contrary, the thread 123 on the storage tube 110 may be a female screw, and the thread 133 on the lid element 130 may be a male screw, which is to be screwed in.

The lid element 130 and the externally equipped opaque writable element 120 are fixed firmly, when the thread 133 on the lid element 130 is screwed together with the thread 123 on the externally equipped opaque writable element 120. The storage tube 110 that is inserted to the externally equipped opaque writable element 120 is enclosed and blocked by the externally equipped opaque writable element 120, the lid element 130, and the gasket 140.

The gasket 140 intervenes between the top of the storage tube 110 and the inner back side 131 of the lid element 130, which seals directly the top opening 111 of the storage tube 110.

Sample storage 100 in embodiment 1 according to the present invention comprises such components as described above.

Carrying of information by the barcodes or two-dimensional codes written in the sample storage 100 according to the present invention is described below. Human visual check of the sample contained in a sample storage 100 and recognition by the recognition system of barcodes and two-dimensional codes according to the present invention are described.

Figure 5:
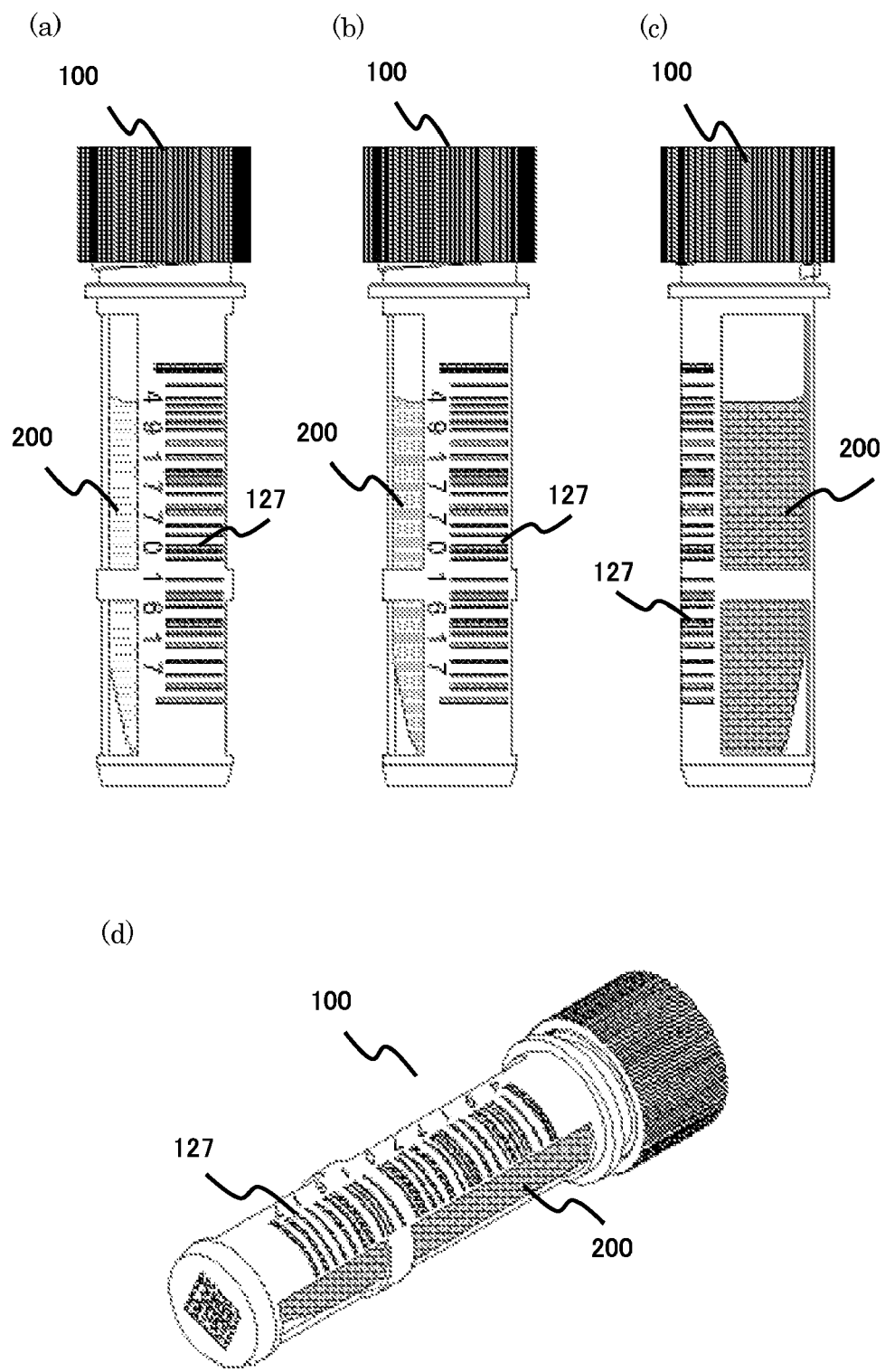
FIG. 5 is a schematic view of an embodiment of the sample storage 100 in various angles showing the status of the sample contained in the sample storage 100.

FIG. 5 shows schematic views at various angles of the sample storage 100 with a sample 200 contained. The sample colors are lighter to deeper in order of FIG. 5 (a), FIG. 5 (b), and FIG. 5 (c).

The externally equipped opaque writable element 120 is made of opaque (for example, black) plastic material, so the storage tube 110 is invisible through a side surface writable area 124. As a result, the color tone and turbidity of sample 200 contained in the storage tube 110 do not affect reading coded information by means of optical reading, as shown in any of FIG. 5 (a), FIG. 5 (b), and FIG. 5 (c). Accordingly, barcodes on the side surface writable area 124 are viewed clearly. As shown in FIG. 5 (d), the storage tube 110 is invisible from the bottom through the bottom surface 126, and the color tone and turbidity of sample 200 contained in the storage tube 110 do not affect reading coded information by means of optical reading. Accordingly, barcodes on the bottom surface writable area 126 are viewed clearly.

Figure 6:
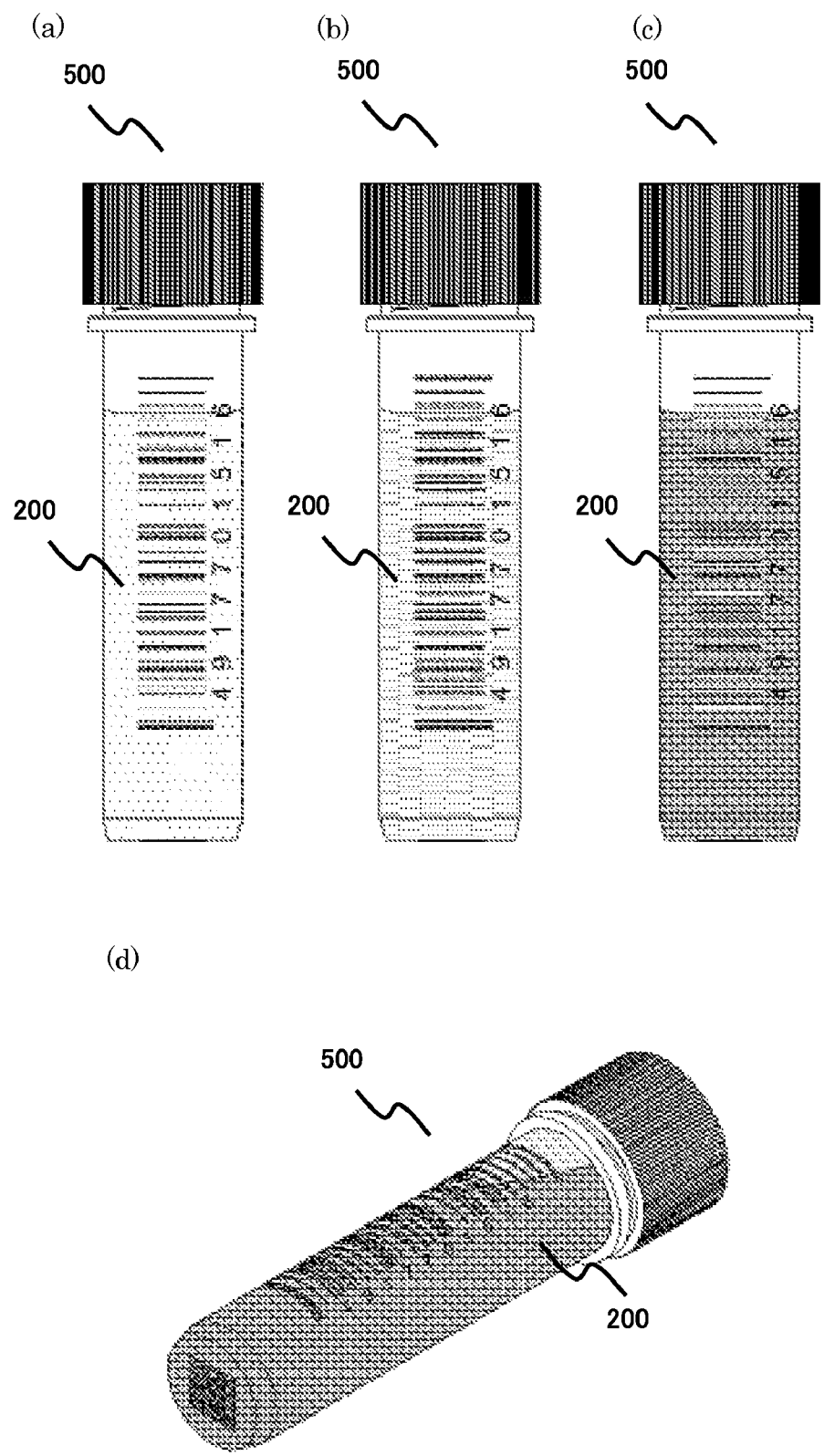
FIG. 6 is a schematic view showing the sample 200 contained in the conventional sample storage 500.

FIG. 6 shows schematic views of a conventional sample storage 500 with a sample 200 contained. The colors of the sample 200 are lighter to deeper in order of FIG. 6 (a), FIG. 6 (b), and FIG. 6 (c). As shown in any of FIG. 6 (a), FIG. 6 (b), and FIG. 6 (c), the color tone and turbidity of the sample 200 contained in the storage tube 500 may affect reading coded information by means of optical reading, so the barcodes printed directly to the outer surface of such storage tubes are superimposed on the sample 200 when barcodes are printed directly, because the sample storage 500 of the conventional art is made of transparent or translucent light-transmissive material. As a result, the sample 200 contained can not be viewed clearly. Accordingly, barcodes on the side surface writable area 124 may not viewed clearly, which may cause false recognition. As shown in FIG. 6 (d), the color tone and turbidity of the sample 200 contained in the storage tube 500 may affect reading coded information by means of optical reading from the bottom. Accordingly, two-dimensional codes on the side surface writable area 126 may not viewed clearly, which may cause false recognition.

As described above, barcodes or two-dimensional codes may not be superimposed on the sample 200, the color tone and turbidity of the sample 200 may not affect reading them, so the sample can be checked visually through the window 125, and barcodes and two-dimensional codes are written to the opaque media (the side surface writable area 124, and the bottom surface writable area 126); accordingly, barcodes and two-dimensional codes may not be superimposed on the sample 200 contained, and the color tone and turbidity of the sample 200 may not affect reading them.

Figure 7:
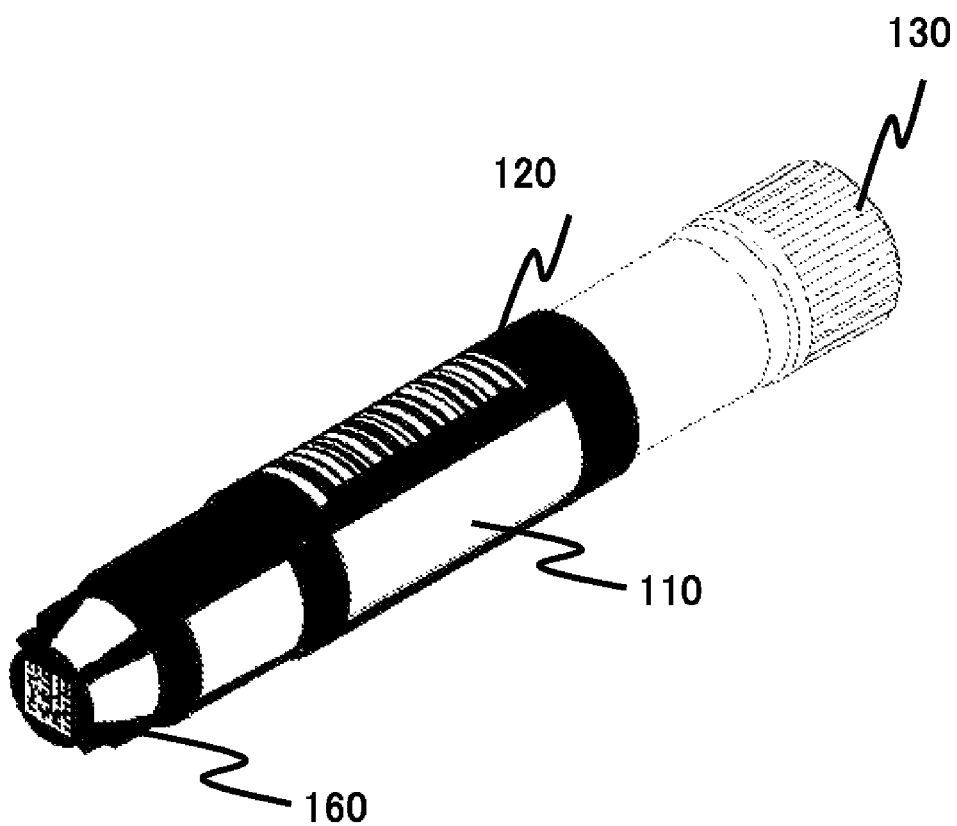
FIG. 7 is a schematic view of an embodiment of the sample storage 100 in which the outline of the externally equipped opaque writable element 120 is round tube shape.
Figure 8:
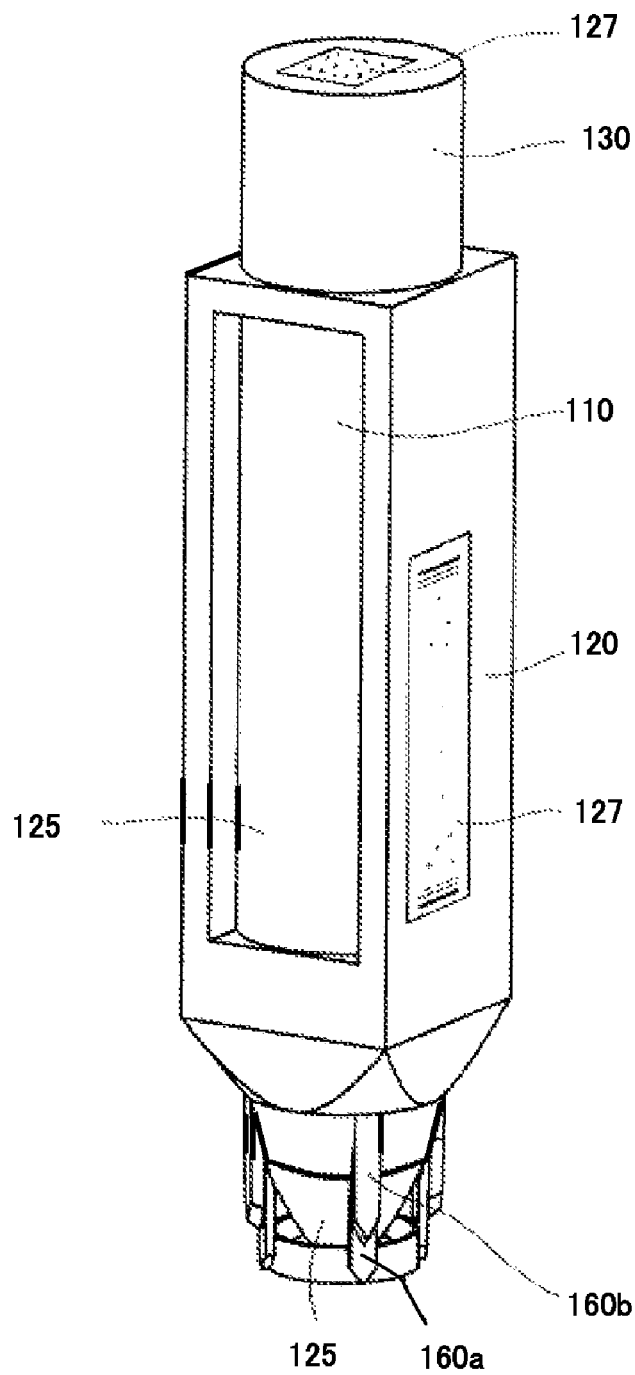
FIG. 8 is a schematic view of an embodiment of the sample storage 100 in which the outline of the externally equipped opaque writable element 120 is a square tube shape.

The outlines of the externally equipped opaque writable element 120 and the lid element 130 of the above-mentioned sample storage 100 are not limited to the outlines shown in FIG. 1. There are various types. The outline shown in FIG. 7 and FIG. 8 are the examples of the variation. The example of the outline of the externally equipped opaque writable element 120 shown in FIG. 7 is a round tube shape, the example of the outline of the externally equipped opaque writable element 120 shown in FIG. 8 is a square tube shape.

Various control methods using the above sample storage 100 can be assumed depending on its use without particular limitation. For example, every data related to the sample storage 100 is checked and controlled by a computer using an allotted index, each measured value is checked with the predetermined high and low limits, and when the data is out of the range, a retry of measurement, a report of detection of errors, or a warning is performed, or instead, another processing such as calculation of the average of multiple measurements and returns the average value can be performed. A human error backup function, such as calibration by checking multiple data and an automatic recovery, can be provided in preparation for such cases that some data is contaminated or damaged under storage or test, using functions for detecting a wrong lid insertion that are set incorrectly and automatically replacing the right lid by comparison check of the lid elements with the externally equipped opaque writable elements in a testing process, and also using functions for saving certain duplicate data to multiple areas. In addition, sample storage 100 may be stored in a sample storage rack, controlled and stored by a computer, automatically picked out when it is used in a test, and then transferred to a specified position to use the sample to the test. Also, the operations to plug a lid element and store to the storage position may be automatically operated by a computer after the test is completed.

Embodiment 2

A sample storage 100a in embodiment 2 according to the present invention is described. The configuration of the embodiment 2 includes a slide plate 150.

Figure 9:
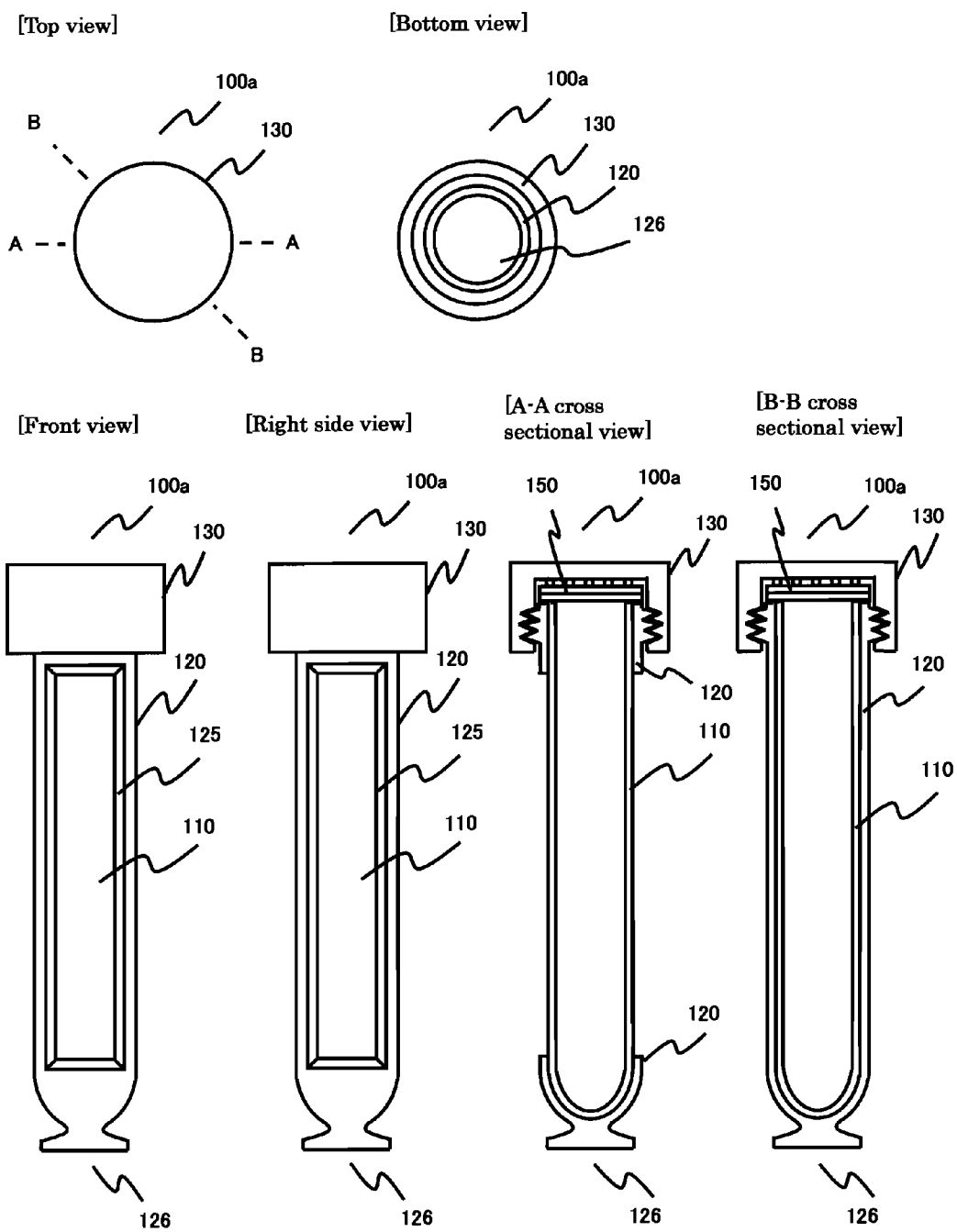
FIG. 9 is a schematic view of the second sample storage 100*a* in embodiment 2.
Figure 10:
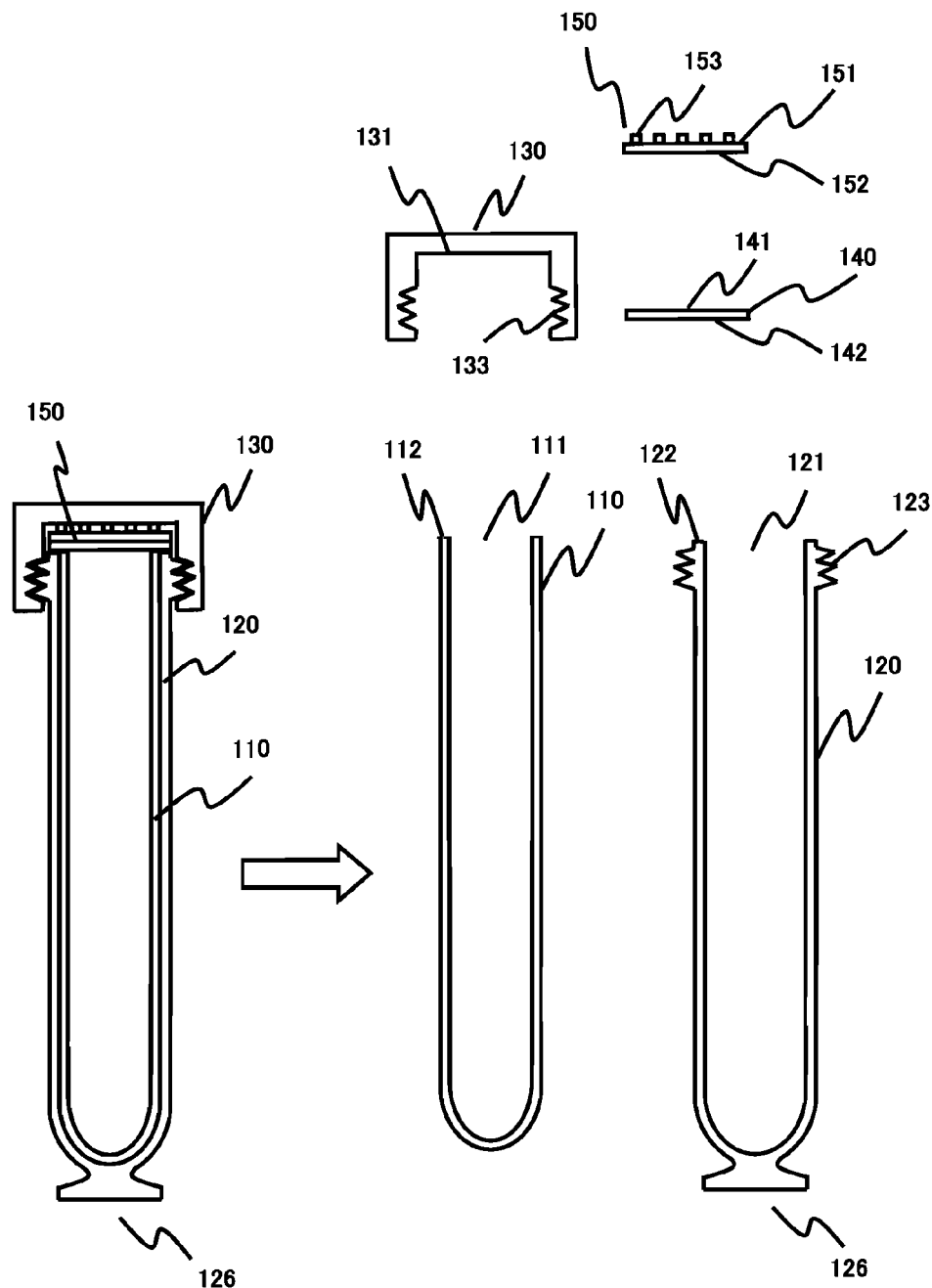
FIG. 10 is an exploded view of the second sample storage 100*a*, which explodes into individual components.

FIG. 9 is a schematic view of a sample storage 100a in embodiment 2 according to the present invention. A front view, right side view, back view, top view, bottom view, and A-A cross-sectional view are shown. FIG. 10 is an exploded view of a sample storage 100a, which explodes into individual components.

As shown in FIG. 9 through FIG. 10, a sample storage 100a in embodiment 2 comprises a storage tube 110, an externally equipped opaque writable element 120, a lid element 130, a gasket 140, and a slide plate 150.

The storage tube 110, the externally equipped opaque writable element 120, the lid element 130 and the gasket 140 of the Embodiment 2 are the same as those of the Embodiment 1, so the explanation of these are omitted here.

The effect of the slide 150 when rotating the lid element 130 is described below.

Figure 11:
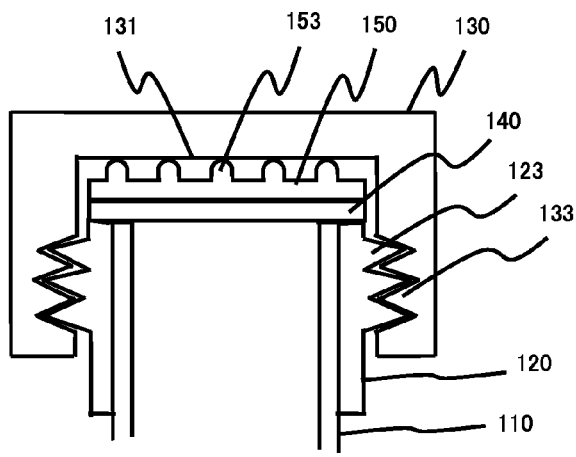
FIG. 11 is a sectional view showing upper portion of the sample storage 100*a* along to the A-A line in FIG. 9 and showing the effect of the slide plate 150 when the lid element 130 is rotated.
Figure 11:
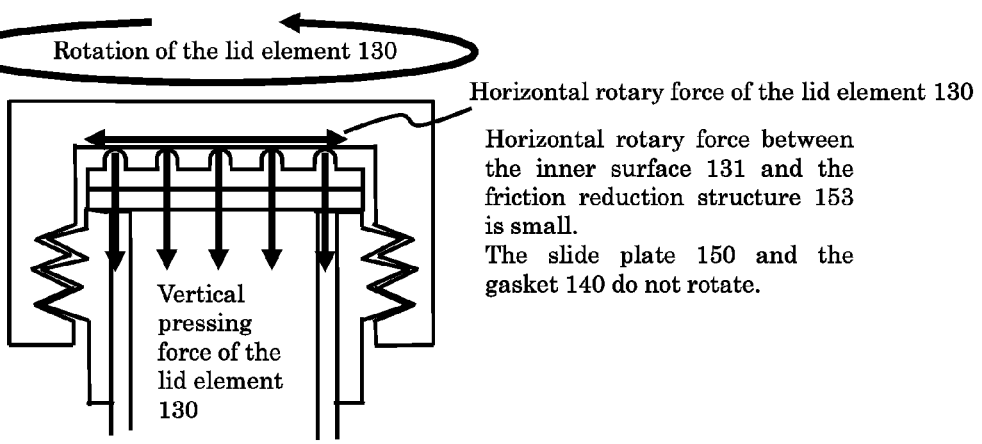

FIG. 11 (a) is a sectional view showing upper portion of the sample storage 100a along to the A-A line in FIG. 9. FIG. 11 (b) is a sectional view showing the effect of the slide plate 150 when the lid element 130 is rotated.

As shown in FIG. 11 (a), the upper surface 141 of the gasket 140 contacts the lower surface 152 of the slide plate 150, the lower surface 142 of the gasket 140 contacts the top opening edge 112 of the storage tube 110 in turn. In this Embodiment 2, the upper edge 112 of the storage tube 110 and the upper edge 122 of the externally equipped opaque writable element 120 are in the same plane, so the gasket 140 also contacts the upper edge 122 of the externally equipped opaque writable element 120 simultaneously.

The slide plate 150 is the plate shape structure inserted between the inner surface 131 of the lid element 130 and the upper surface 141 of the gasket 140. The upper surface 151 of the slide plate 150 contacting to the inner surface 131 of the lid element 130 includes the friction reduction structure 153 for reducing the horizontal friction generated between the inner surface 131 of the lid element 130.

In this Embodiment 2, the friction reduction structure 153 is plural small prickles for reducing the contacting area to the facing surface.

As shown in FIG. 11 (b), if the lid element 130 is screwed into the externally equipped opaque writable element 120, the horizontal rotary force and the vertical pressing force are generated on the inner surface 131 of the lid element 130 simultaneously.

Figure 12:
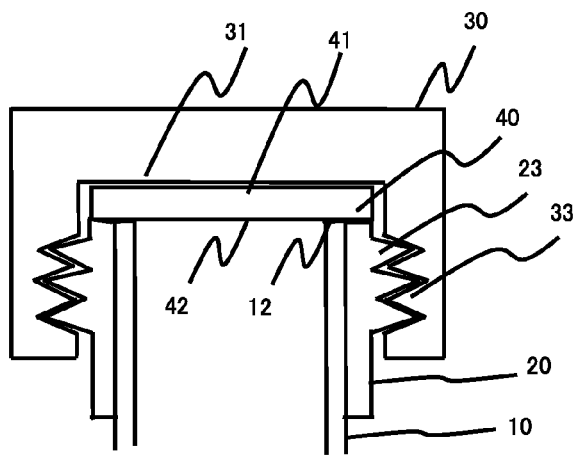
FIG. 12 is a sectional view showing an upper portion of the conventional sample storage and showing the effect of the conventional gasket when the conventional lid element is rotated.
Figure 12:
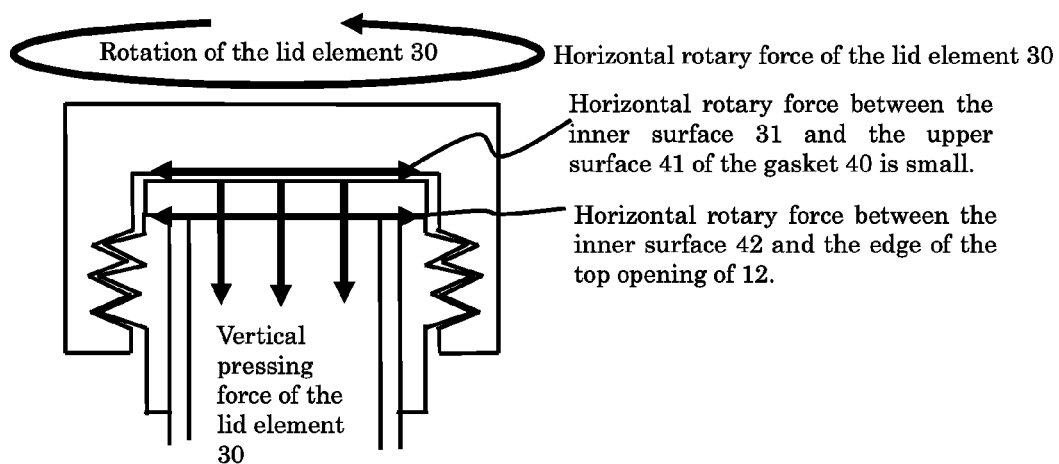

FIG. 12 is a sectional view showing upper portion of the conventional sample storage and showing the effect of the conventional gasket when the conventional lid element is rotated. The horizontal rotary force and the vertical pressing force are transmitted to the gasket 140 via the slide plate 150 because there is the slide plate 150 including the friction reduction structure facing to the inner surface 131 of the lid element 130. The slide plate 150 keeps stationary status without co-motion to the rotation of the lid element 130 due to the reduction of the friction by the friction reduction structure 153. In other words, the lid element 130 remains idle in the horizontal direction. As shown above, the horizontal rotary force is not transmitted to the slide plate 150 and the gasket 140 though the horizontal rotary force and the vertical pressing force are generated by the lid element 130 simultaneously.

On the contrary, as shown in FIG. 11 (b), the friction reduction structure 153 reduces the horizontal rotary force, but does not influence the vertical pressing force, and the vertical pressing force is transmitted to the slide plate 150 and gasket 140 directly. In other words, the essential purpose of the lid element 130 for sealing the top opening 111 of the storage tube 110 can be achieved by pressing the gasket 140 to the top opening 111 of the storage tube 110.

As shown above, the slide plate 150 controls the motion of the gasket 140 to pressing down vertically to the top opening 112 of the storage tube 110, not to rotate horizontally, so the gasket 140 is not damaged or broken even though there are prickles on the top opening of the storage container 110, and the gasket 140 can seal the top opening 112 of the storage tube 110.

Hereinafter, the conventional case in which the slide plate 150 is not utilized is described for the comparison. FIG. 12 (a) is a sectional view showing the upper portion of the conventional sample storage without the slide plate 150 of the present invention. FIG. 12 (b) is a sectional view showing the force generated in the parts when the lid element 130 is rotated.

As shown in FIG. 12 (b), if the lid element 130 is screwed into the externally equipped opaque writable element 120, the horizontal rotary force and the vertical pressing force are generated on the inner surface 131 of the lid element 130, and a large rotary friction is generated on the upper surface 141 of gasket 140 because the whole inner surface 131 of the lid element 130 contacts the upper surface 141 of the gasket 140. As shown above, both the horizontal rotary force and the vertical pressing force generated by the lid element 130 are transmitted to the gasket 140, and the gasket 140 can rotate due to the horizontal rotary force. If the gasket 140 rotates, the gasket 140 can be damaged or broken by the prickles on the top opening 112 of the storage tube 110.

It is explained by comparison of FIG. 11 and FIG. 12, according to the second sample storage 100a of the present invention the slide plate 150 including the friction reduction structure 153 controls so that only the vertical pressing force is transmitted to the gasket 140 and the horizontal rotary force is not transmitted to the gasket 140 though the horizontal rotary force and the vertical pressing force are generated simultaneously by the lid element 130 when the lid element 130 is screwed into the externally equipped opaque writable element 120. The gasket 140 is not damaged or broken even though there are prickles on the top opening of the storage container 110, and the gasket 140 can seal the top opening 112 of the storage tube 110.

Embodiment 3

A sample storage 100b in embodiment 3 according to the present invention is described. The configuration of the embodiment 3 includes a slide plate 150b between the gasket 140 and the inner surface of the lid element 130b, the friction reduction structure 132b being on the inner surface of the lid element 130b.

Figure 13:
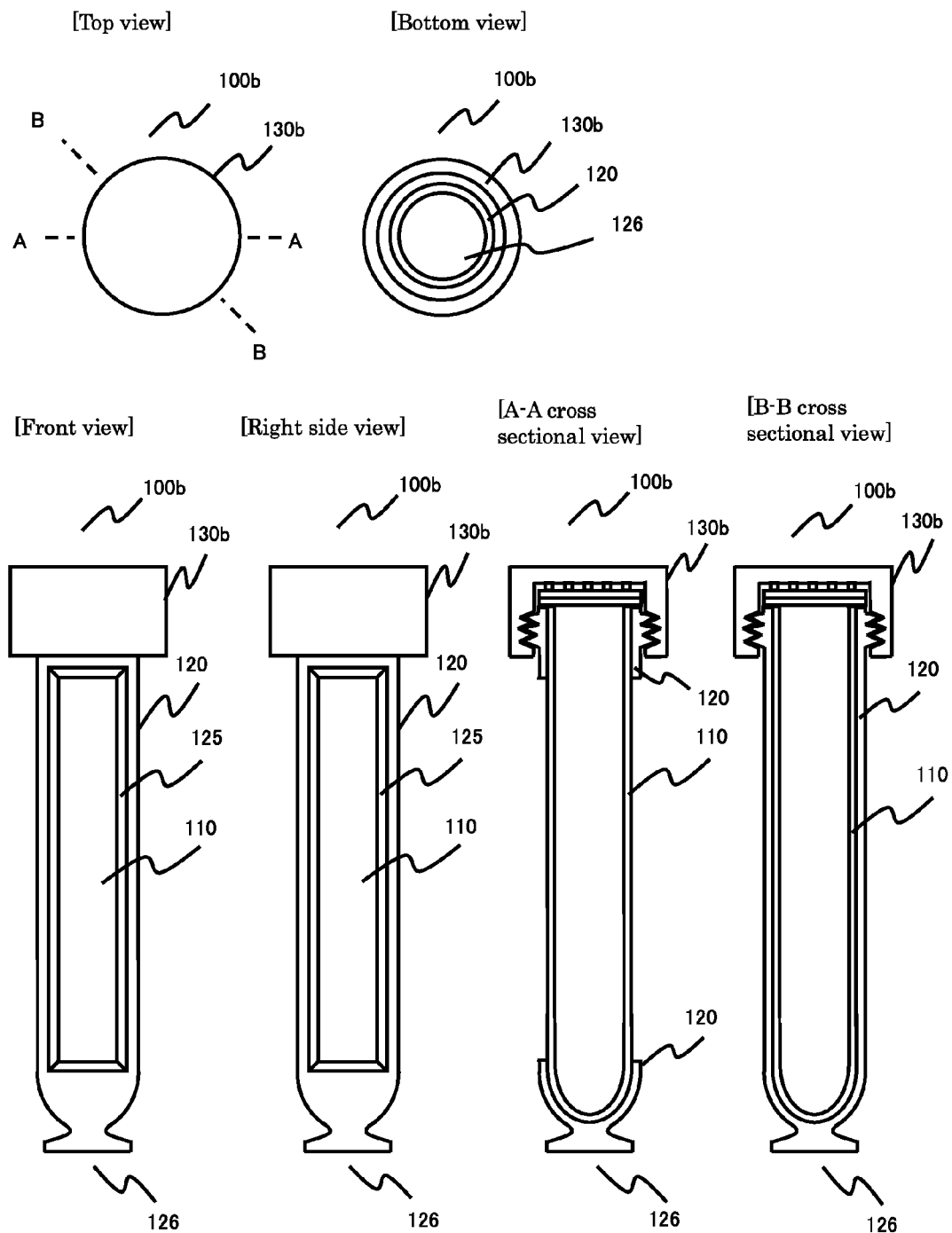
FIG. 13 is a schematic view of the third sample storage 100*b* in embodiment 3.
Figure 14:
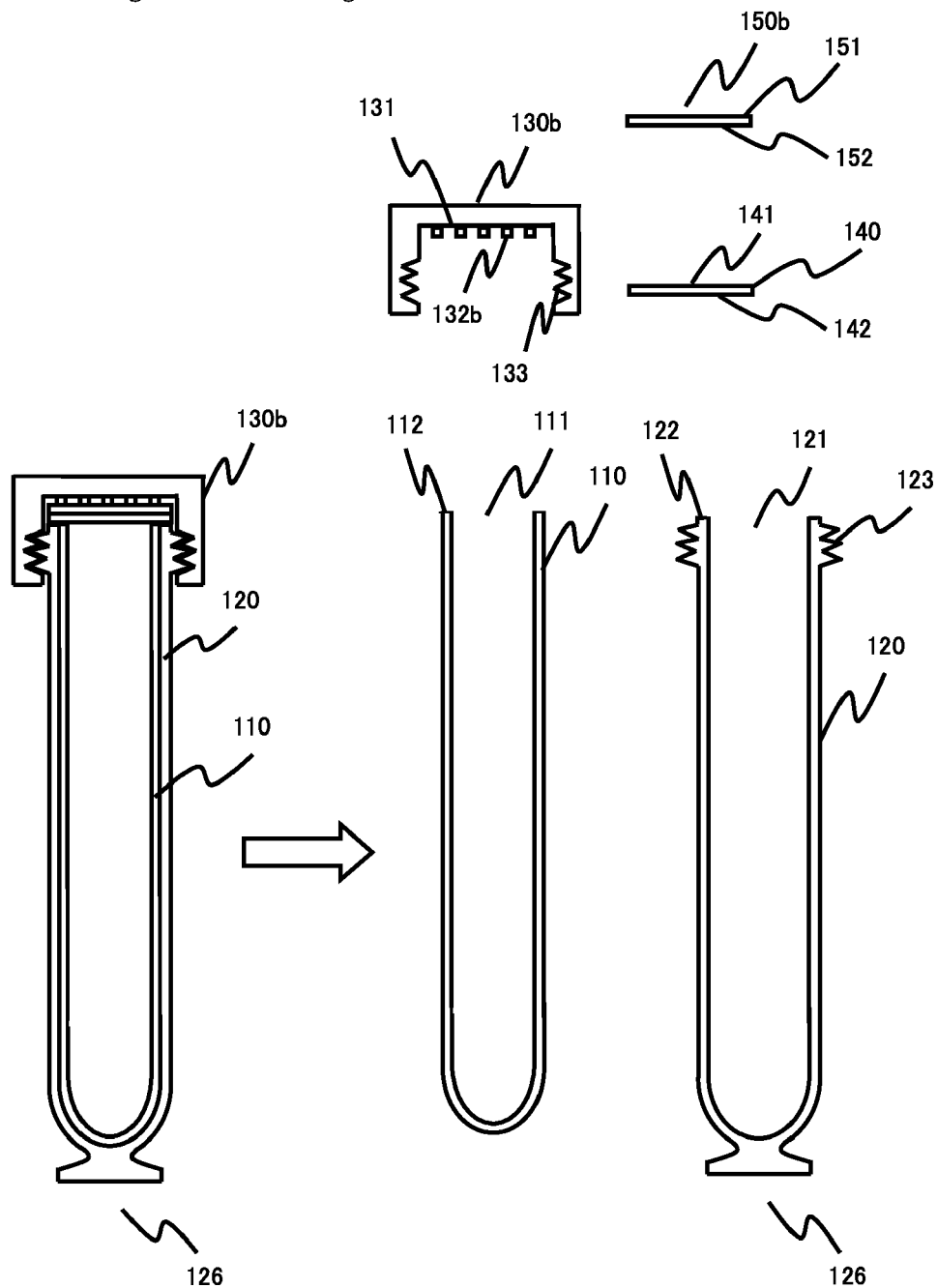
FIG. 14 is an exploded view of the third sample storage 100*b*, which explodes into individual components.

FIG. 13 is a schematic view of the third sample storage 100b in embodiment 3 according to the present invention. A front view, right side view, back view, top view, bottom view, A-A cross-sectional view, and B-B cross-sectional view are shown. FIG. 14 is an exploded view of a sample storage 100b, which explodes into individual components.

As shown in FIG. 13, the third sample storage 100b in embodiment 3 comprises a storage tube 110, an externally equipped opaque writable element 120, a lid element 130, a gasket 140, and a slide plate 150b. The storage tube 110, the externally equipped opaque writable element 120 and the gasket 140 except for the lid element 130b and the slide plate 150b are the same as those of the Embodiment 1, so the explanation of these are omitted here.

As shown in FIG. 14, the same as the Embodiment 2, the lid element 130b is the lid for sealing the top opening 111 of the storage tube 110, the friction reduction structure 132b is included in the inner surface 131 of the lid element 130 in this Embodiment 3. In this Embodiment 3, the same as Embodiment 2, the friction reduction structure 132b is a plurality of prickles for reducing the contacting area to the facing surface.

On the other hand, the slide plate 150b is the plate shape structure inserted between the inner surface 131 of the lid element and the upper surface 141 of the gasket 140 the same as Embodiment 2, however, the friction reduction structure 153 is not included in the slide plate 150b.

The effect of the lid element 130b and slide plate 150b during rotating the lid element 130b is described below.

Figure 15:
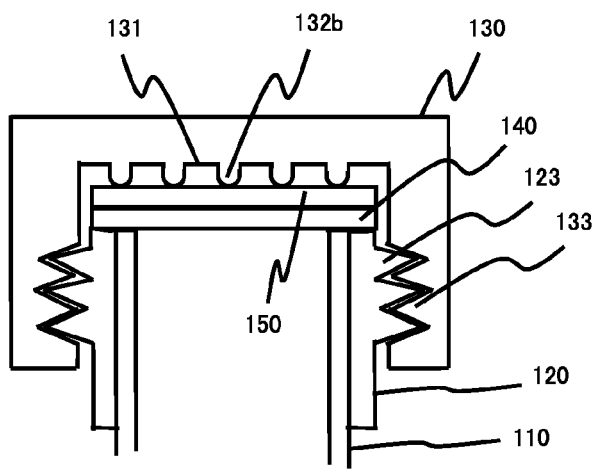
FIG. 15 is a sectional view showing upper portion of the sample storage 100*b* along to the A-A line in FIG. 13 and showing the effect of the friction reduction structure 132*b* when the lid element 130*b* is rotated.
Figure 15:
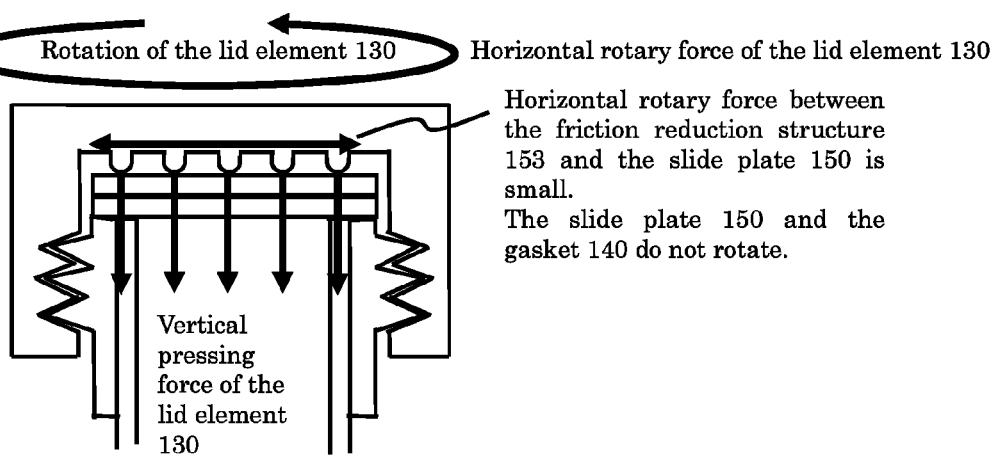

FIG. 15 (a) is a cross sectional view showing upper portion of the sample storage 100b along to the A-A line in FIG. 14. FIG. 15 (b) is a cross sectional view showing the effect of the friction reduction structure 132b when the lid element 130b is rotated.

As shown in FIG. 15, if the lid element 130b is screwed into the externally equipped opaque writable element 120, the horizontal rotary force and the vertical pressing force are generated on the inner surface 131 of the lid element 130b simultaneously. There is the friction reduction structure 132b in the inner surface 131 of the lid element 130b so the lid element 130b does not contacted the slide plate 150b directly, and the lid element 130b contacts the slide plate 150b via the friction reduction structure 132b.

The horizontal rotary force is not transmitted to the slide plate 150b and the gasket 140 due to the reduction of the friction by the friction reduction structure 132b, so the slide plate 150b and the gasket 140 keep stationary status without co-motion with the rotation of the lid element 130b. In other words, the slide plate 150b remains idle in the horizontal direction.

On the contrary, the vertical pressing force is transmitted to the gasket 140 via the slide plate 150b because the friction reduction structure 132b does not influence the vertical pressing force. The essential purpose of the lid element 130b for sealing the top opening 111 of the storage tube 110 can be achieved by pressing the gasket 140 to the top opening 111 of the storage tube 110.

According to the sample storage 100b of this Embodiment 3, only the vertical pressing force is transmitted to the gasket 140 and the horizontal rotary force is not transmitted to the gasket 140 by applying the lid element 130b including the friction reduction structure 132b onto the upper surface of the lid element 130b. The gasket 140 is not damaged or broken even though there are prickles on the top opening of the storage container 110, and the gasket 140 can seal the top opening 112 of the storage tube 110.

Embodiment 4

A sample storage 100c in embodiment 4 according to the present invention is described. The configuration of the embodiment 4 includes a slide plate between the gasket 140 and the inner surface of the lid element, the friction reduction structure 153c onto the lower surface 152 facing the upper surface of gasket 140.

Figure 16:
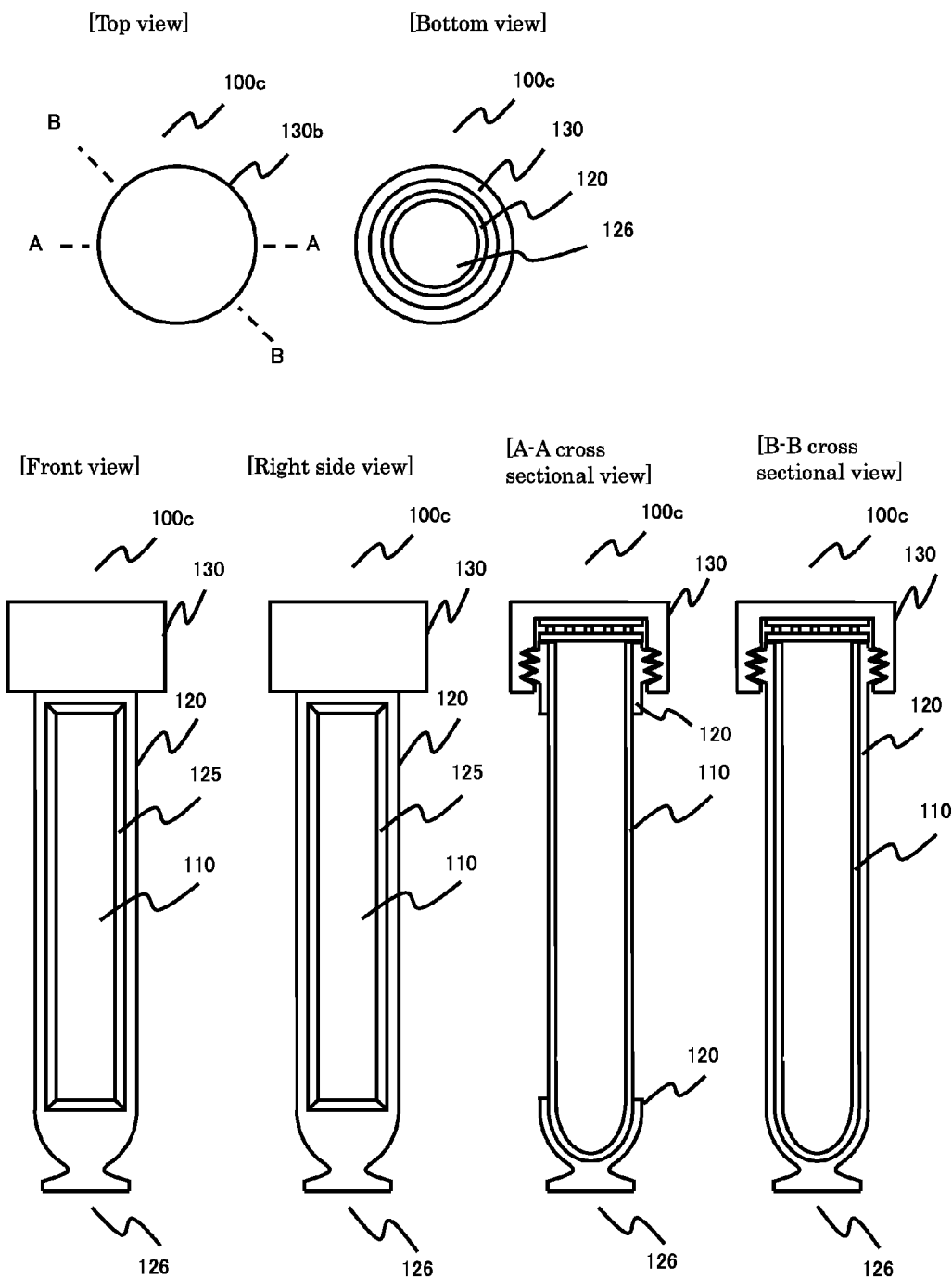
FIG. 16 is a schematic view of the fourth sample storage 100*c* in embodiment 4.
Figure 17:
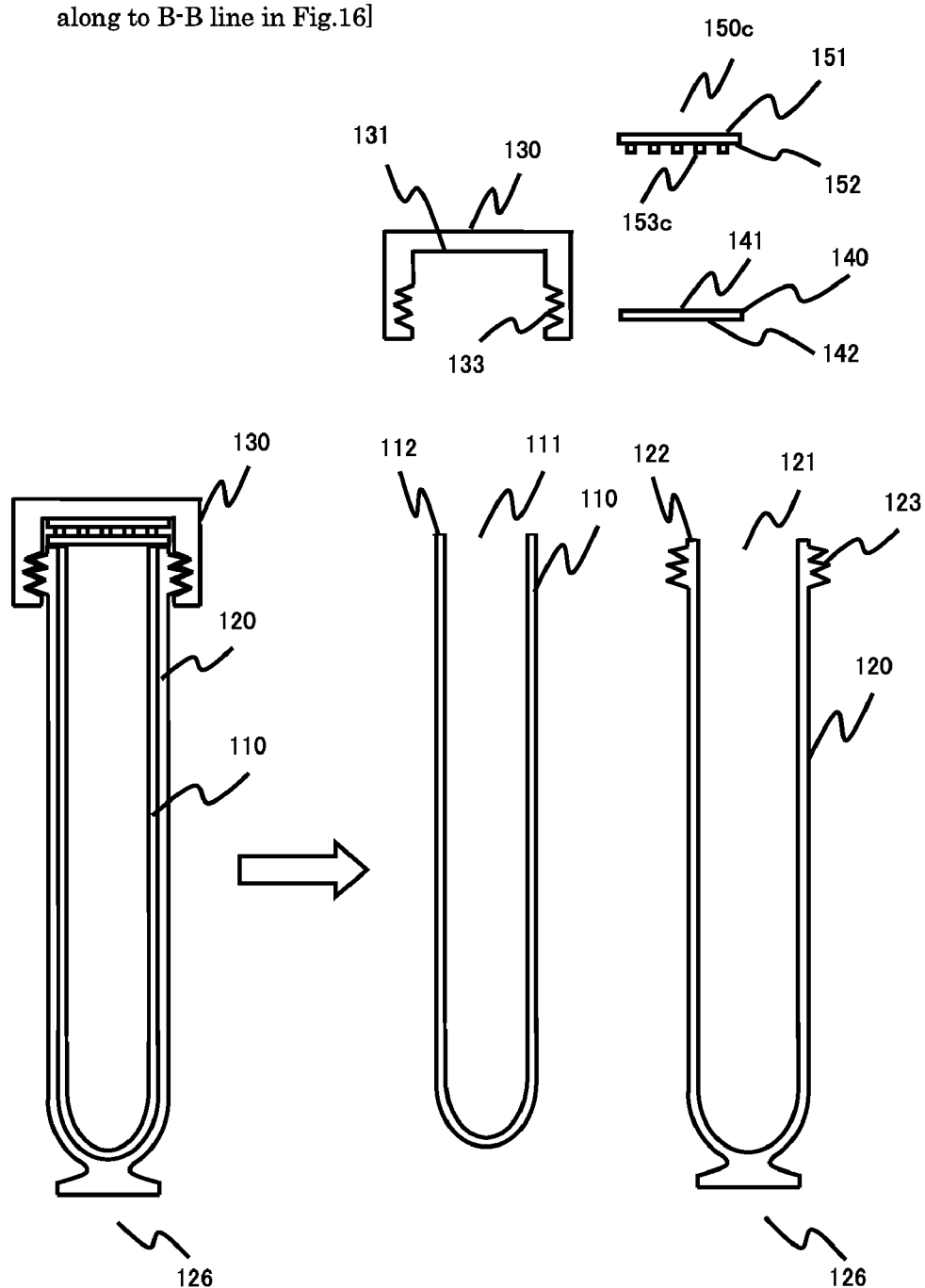
FIG. 17 is an exploded view of the fourth sample storage 100*c*, which explodes into individual components.

FIG. 16 is a schematic view of the third sample storage 100c in embodiment 4 according to the present invention. A front view, right side view, back view, top view, bottom view, A-A cross-sectional view, and B-B cross-sectional view are shown. FIG. 17 is an exploded view of a sample storage 100c, which explodes into individual components.

As shown in FIG. 16, the fourth sample storage 100c in embodiment 4 comprises a storage tube 110, an externally equipped opaque writable element 120, a lid element 130, a gasket 140, and a slide plate 150c. The storage tube 110, the externally equipped opaque writable element 120, the lid element 130 and the gasket 140 except for the slide plate 150c are the same as those of the Embodiment 1, so the explanation of these are omitted here.

The slide plate 150c is the plate shape structure inserted between the inner surface 131 of the lid element and the upper surface 141 of the gasket 140 the same as Embodiment 1, however, the friction reduction structure 153c for reducing the horizontal friction is included in the lower surface 152 of the slide plate 150c. In this Embodiment 4, the same as Embodiment 1, the friction reduction structure 153c is a plurality of prickles for reducing the contacting area to the facing surface.

The effect of the slide plate 150c during rotating the lid element 130 is described below.

Figure 18:
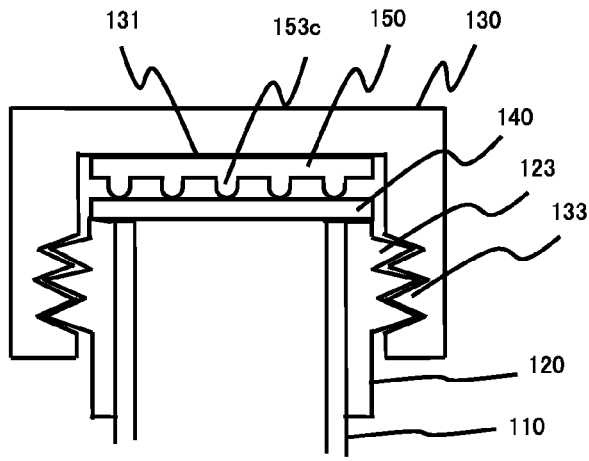
FIG. 18 is a sectional view showing an upper portion of the sample storage 100*c* along to the A-A line in FIG. 16 and showing the effect of the friction reduction structure 153*c* when the lid element 130*c* is rotated.
Figure 18:
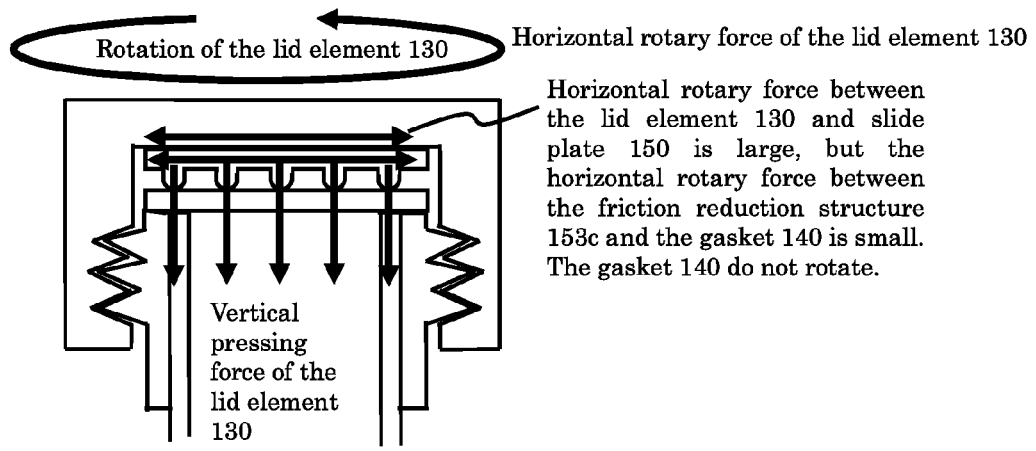

FIG. 18 (a) is a cross sectional view showing upper portion of the sample storage 100c along to the A-A line in FIG. 16. FIG. 18 (b) is a cross sectional view showing the effect of the friction reduction structure 153c when the lid element 130 is rotated.

If the lid element 130 is screwed into the externally equipped opaque writable element 120, the horizontal rotary force and the vertical pressing force are generated on the inner surface 131 of the lid element 130 simultaneously. There is the friction reduction structure 153c onto the lower surface 152 of the slide plate 150c facing the upper surface 141 of the gasket, so the horizontal rotary force and the vertical pressing force from the inner surface 131 of the lid element are transmitted to the gasket 140 via the slide plate 150c.

However, there is the friction reduction structure 153c on the slide plate 150c. The slide plate 150c can rotate by the horizontal rotary force because the whole surface of the slide plate 150c is contacted to the facing lid element 130, but the horizontal rotary force is not transmitted to the gasket 140 because there is the friction reduction structure 153c between the slide plate 150c and the gasket 140, so the gasket 140 keeps stationary status without co-motion with the rotation of the lid element 130. In other words, the gasket 140 remains idle in the horizontal direction. As shown above, the horizontal rotary force is not transmitted to the gasket 140.

On the contrary, the vertical pressing force is transmitted to the gasket 140 via the slide plate 150c because the friction reduction structure 153c does not influent on the vertical pressing force. The essential purpose of the lid element 130 for sealing the top opening 111 of the storage tube 110 can be achieved by pressing the gasket 140 to the top opening 111 of the storage tube 110.

According to the sample storage 100c of this Embodiment 4, only the vertical pressing force is transmitted to the gasket 140 and the horizontal rotary force is not transmitted to the gasket 140 by applying the slide plate 150d including the friction reduction structure 153c on the lower the surface of the slide plate 150c. The gasket 140 is not damaged or broken even though there are prickles on the top opening of the storage container 110, and the prickles are not broken. The gasket 140 can seal the top opening 112 of the storage tube 110.

According to the sample storage 100d of this Embodiment 5, only the vertical pressing force is transmitted to the gasket 140d and the horizontal rotary force is not transmitted to the gasket 140d by applying the gasket 140d including the friction reduction structure 143d on the upper surface 141 of the gasket 140d. The gasket 140d is not damaged or broken even though there are prickles on the top opening of the storage container 110, and the prickles are not broken. The gasket 140d can seal the top opening 112 of the storage tube 110.

Embodiment 5

A sample storage 100d in embodiment 5 according to the present invention is described. The configuration of the embodiment 5 includes a friction reduction structure 143d for reducing the coefficient of the friction between the upper surface of the gasket 140 and the inner surface of the lid element.

Figure 19:
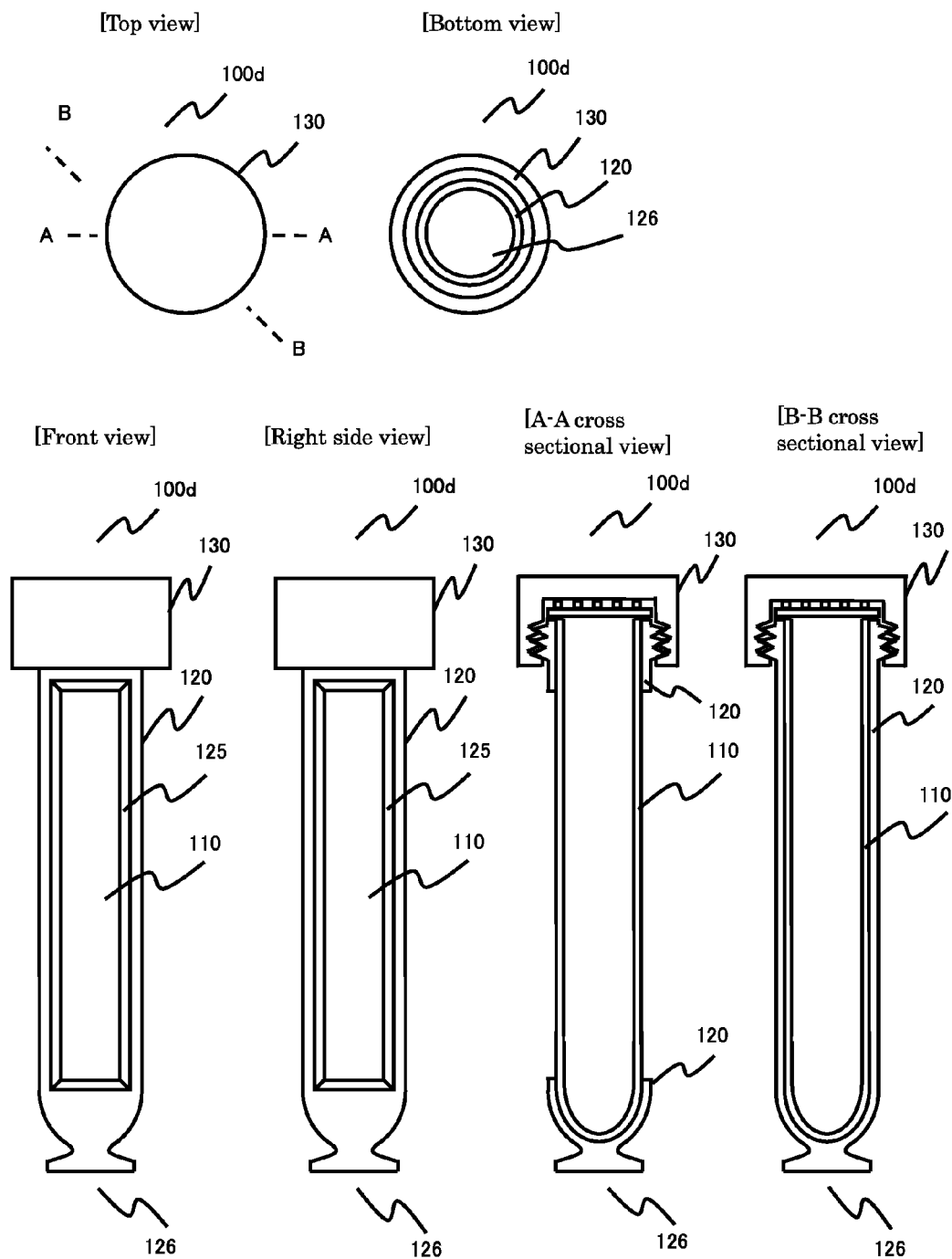
FIG. 19 is a schematic view of the fifth sample storage 100*d* in embodiment 5.
Figure 20:
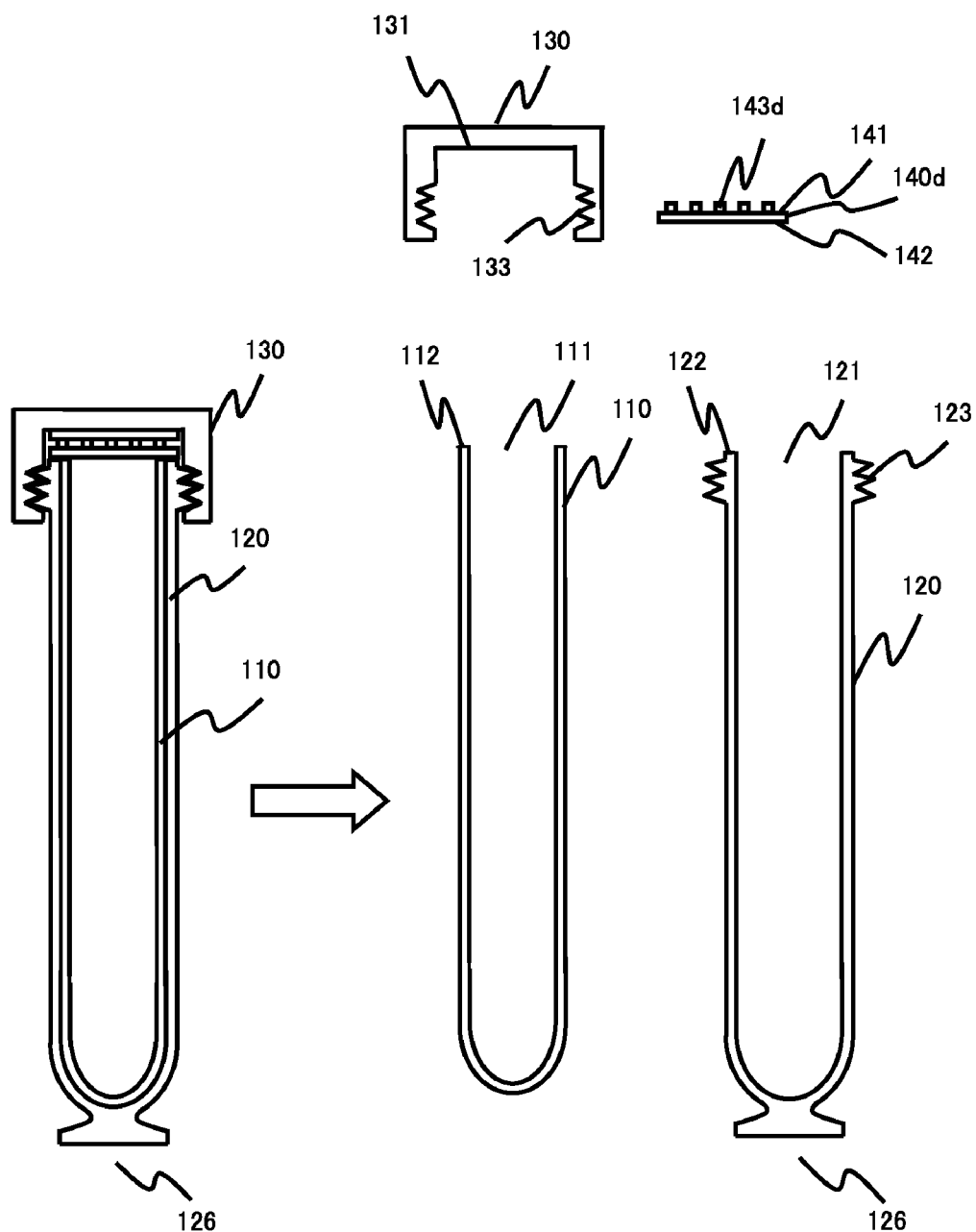
FIG. 20 is an exploded view of the fifth sample storage 100*d*, which explodes into individual components.

FIG. 19 is a schematic view of the third sample storage 100d in embodiment 5 according to the present invention. A front view, right side view, back view, top view, bottom view, A-A cross-sectional view, and B-B cross-sectional view are shown. FIG. 20 is an exploded view of a sample storage 100d, exploded into individual components.

As shown in FIG. 19, the fifth sample storage 100d in embodiment 5 comprises a storage tube 110, an externally equipped opaque writable element 120, a lid element 130, and a gasket 140d. The storage tube 110, the externally equipped opaque writable element 120, the lid element 130 except for the gasket 140d are the same as those of the Embodiment 1, so the explanation of these are omitted here.

The gasket 140d for sealing the top opening 111 of the storage tube 110 exists between the upper surface of the storage tube 110 and the inner surface 131 of the lid element 130 the same as Embodiment 1, Embodiment 2 and Embodiment 3, however, the friction reduction structure 143d for reducing the coefficient of the horizontal friction is included in the upper surface 141 of the gasket 140d. In this Embodiment 5, the friction reduction structure 143d is a plurality of prickles for reducing the contacting area to the facing surface.

The effect of the gasket 140d during rotating the lid element 130 is described below.

Figure 21:
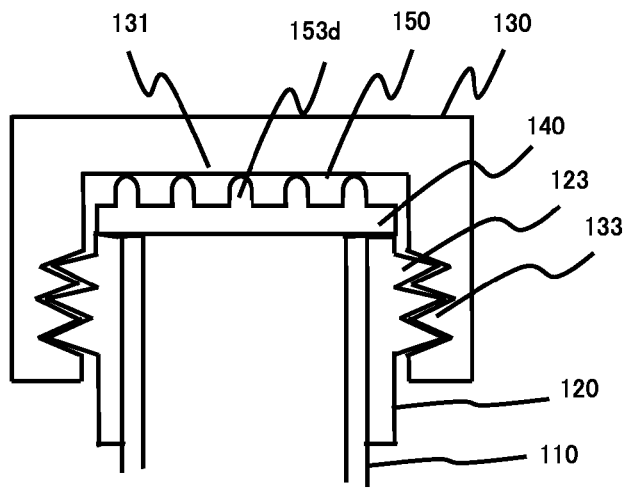
FIG. 21 is a sectional view showing an upper portion of the sample storage 100*d* along to the A-A line in FIG. 19 and showing the effect of the friction reduction structure 143*d* when the lid element 130*d* is rotated.
Figure 21:
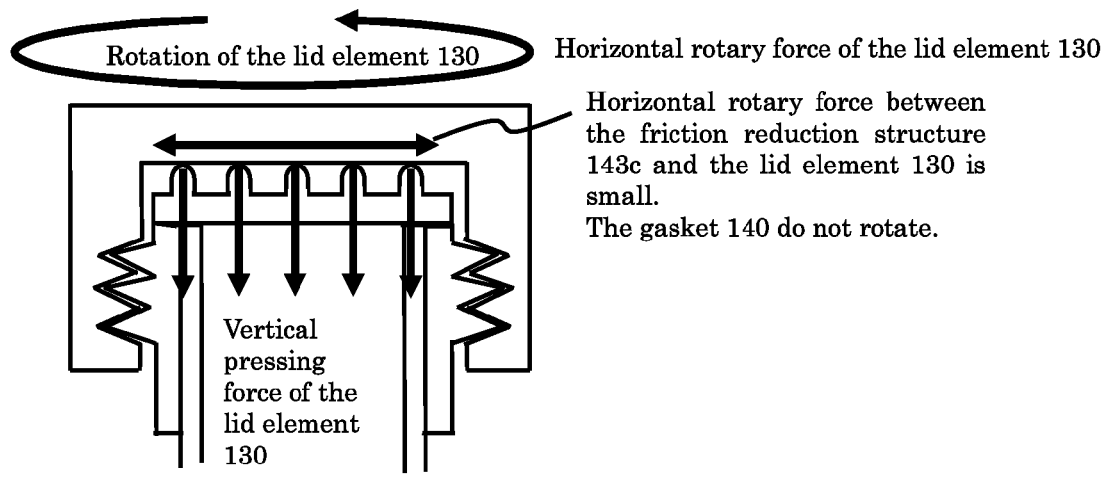
Figure 22:
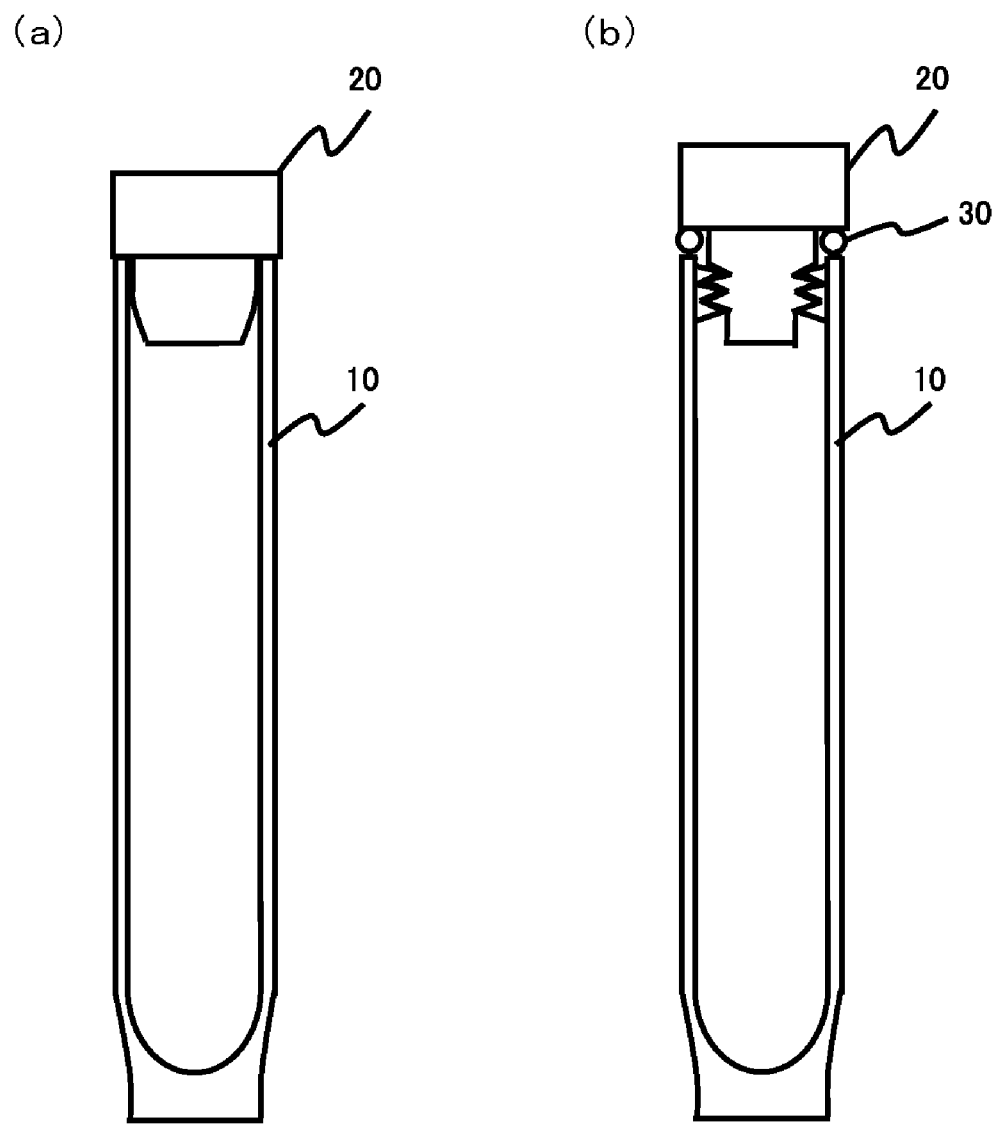
FIG. 22 is a schematic view of the conventional sample storage 10.
Figure 23:
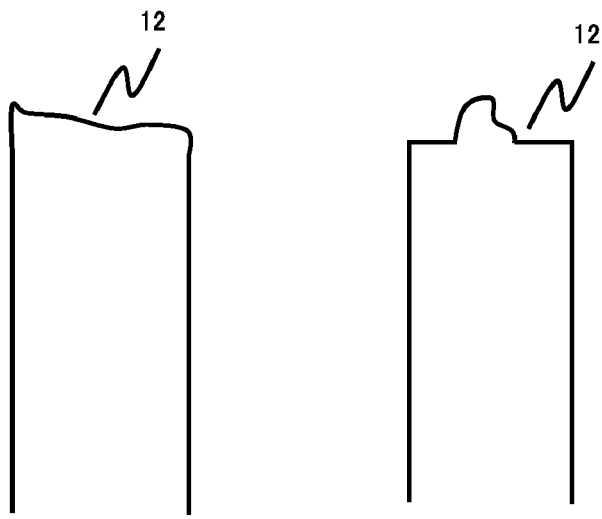
FIG. 23 is a schematic view showing the motion of each part when conventional lid element 30 is installing to the conventional sample storage 10.
Figure 23:
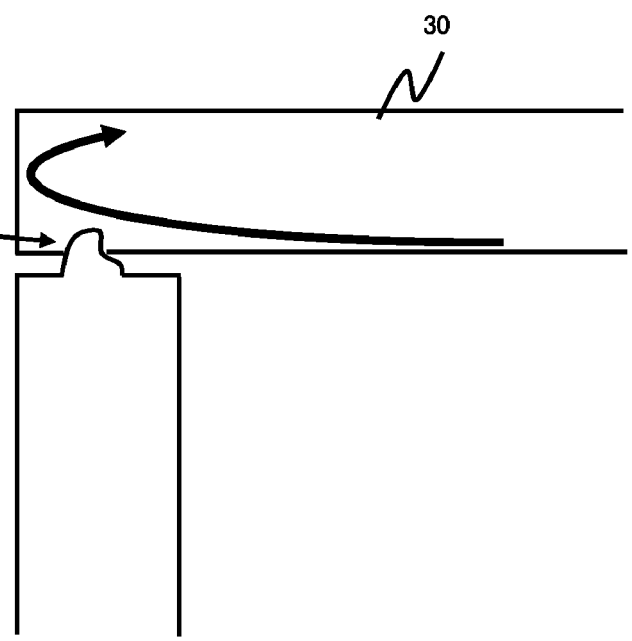

FIG. 21 (a) is a cross sectional view showing upper portion of the sample storage 100d along to the A-A line in FIG. 20. FIG. 21 (b) is a cross sectional view showing the effect of the friction reduction structure 143d of the gasket 140 when the lid element 130 is rotated.

If the lid element 130 is screwed into the externally equipped opaque writable element 120, the horizontal rotary force and the vertical pressing force to the gasket 140d are generated on the inner surface 131 of the lid element 130 simultaneously. The horizontal rotary force and the vertical pressing force from the inner surface 131 of the lid element 130 are transmitted to the gasket 140d. However, there is the friction reduction structure 143d in the upper surface 141 of the gasket 140d for reducing the horizontal rotary force, so the horizontal rotary force is not transmitted to the gasket 140d because there is the friction reduction structure 143d between the lid element 130 and the gasket 140d. The gasket 140d keeps stationary status without co-motion with the rotation of the lid element 130. In other words, the gasket 140d remains idle in the horizontal direction. As shown above, the horizontal rotary force is not transmitted to the gasket 140d.

On the contrary, the vertical pressing force is transmitted to the gasket 140d because the friction reduction structure 143d does not influent on the vertical pressing force. The essential purpose of the lid element 130 for sealing the top opening 111 of the storage tube 110 can be achieved by pressing the gasket 140d to the top opening 111 of the storage tube 110.

According to the sample storage 100d of this Embodiment 5, only the vertical pressing force is transmitted to the gasket 140d and the horizontal rotary force is not transmitted to the gasket 140d by applying the gasket 140d including the friction reduction structure 143d on the upper surface 141 of the gasket 140d. The gasket 140d is not damaged or broken even though there are prickles on the top opening of the storage container 110, and the prickles are not broken. The gasket 140d can seal the top opening 112 of the storage tube 110.

While some preferable embodiments of the sample storage according to the present invention are described above, it should be understood that various changes are possible, without deviating from the technical scope according to the present invention. Therefore, the technical scope according to the present invention is limited only by the claims attached.

INDUSTRIAL APPLICABILITY

A sample storage according to the present invention can be extensively used for storing a large number of samples. For example, it can be used as a sample storage for enclosing and storing drug samples. Also, it can be used as a sample storage for storing such samples that hold gene information of DNA in medicine field.

The invention claimed is:
1. A sample storage, comprising;
a storage tube having a top opening, which is made of light-transmissive material to enable a contained sample to be observed,
an externally equipped opaque writable element used as a medium to which coded information that can be read by means of optical reading already has been written directly, which is assembled outside by covering said storage tube throughout from the bottom surface to the side surface,
a lid element covering the top opening of the storage tube by pressing the inner surface of the lid element or a gasket to the top opening of the storage tube, wherein the lid element can be screwed with or combined with the externally equipped opaque writable element, cannot be screwed with or combined with the inner surface of the top opening of the storage tube directly,
and at least one window as an opening in the side surface of said externally equipped opaque writable element, provided in an area other than the write area where said coded information is written, which enables said sample contained to be observed;
the externally equipped opaque writable element covers the side and bottom of the storage tube without airtightness,
and which enables said coded information written to said externally equipped opaque writable element to be read, and said sample contained to be observed through said window.

2. A sample storage as claimed in claim 1, in which said coded information is written to both said coded information write areas that correspond to the bottom surface and the side surfaces of said storage tube.

3. A sample storage as claimed in claim 1, in which said externally equipped opaque writable element is made of opaque plastic material to disable said storage tube being viewed through said coded information write area, so that the color tone and turbidity of said sample contained in said storage tube do not affect reading said coded information by means of said optical reading.

4. A sample storage as claimed in any of claim 1, in which the material color of said externally equipped opaque writable element is the same as the color to be expressed as bars or dots of said coded information, and said coded information directly written to said externally equipped opaque writable element is expressed by changing the color of the area other than bars or dots of said coded information to a different color from said material color.

5. A sample storage as claimed in any of claim 1, in which the material color of said externally equipped opaque writable element is different from the color to be expressed as bars or dots of said coded information, and said coded information directly written to said externally equipped opaque writable element is expressed by changing the color of the area of bars or dots of said coded information to the color to be expressed as bars or dots of said coded information.

6. A sample storage as claimed in any of claim 1, further comprising:
a gasket for facing directly to the top opening of said storage container;
a slide plate installed between the inner surface of said lid element and said gasket for blocking the transmission of the horizontal rotary force of said lid element to said gasket;
wherein the slide plate controls so that only the vertical pressing force is transmitted to the gasket, but the horizontal rotary force is not transmitted to the gasket though the vertical pressing force and the horizontal rotary force are generated simultaneously on the inner surface of the lid element when the lid element is screwed into or fitted into the externally equipped opaque writable element.

7. A sample storage as claimed in claim 6, wherein said slide plate comprises a friction reduction structure on the surface facing the inner surface of the lid element for reducing the horizontal friction between the slide plate and the inner surface of the lid element, the transmission of the horizontal rotary force generated by the lid element to the slide plate is blocked by the friction reduction structure.

8. A sample storage as claimed in claim 6, wherein the lid element comprises a friction reduction structure on the inner surface for reducing the horizontal friction between the slide plate and the inner surface of the lid element, and the transmission of the horizontal rotary force generated by the lid element to the slide plate is blocked by the friction reduction structure.

9. A sample storage as claimed in any of claim 1, further comprising:
   a gasket for facing directly to the top opening of said storage container;
   wherein the gasket plate comprises a friction reduction structure on the surface facing the inner surface of the lid element for reducing the horizontal friction between the gasket and the inner surface of the lid element, the transmission of the horizontal rotary force generated by the lid element to the gasket is blocked by the friction reduction structure, only the pressing force generated by the lid element is transmitted to the gasket.

10. A sample storage as claimed in claim 9, wherein the friction reduction structure is a plurality of small prickles for reducing the contacting area to the facing surface.

11. A sample storage as claimed in any of claim 1, wherein the lid element can be screwed with or combined with the storage container instead of the externally equipped opaque writable element, further comprising:
   a gasket for facing directly to the top opening of said storage container;
   a slide plate installed between the inner surface of said lid element and said gasket for blocking the transmission of the horizontal rotary force of said lid element to said gasket;
   wherein the gasket plate comprises a friction reduction structure on the surface facing the inner surface of the lid element for reducing the horizontal friction between the gasket and the inner surface of the lid element, and the transmission of the horizontal rotary force generated by the lid element to the gasket is blocked by the friction reduction structure, only the pressing force generated by the lid element is transmitted to the gasket.

12. A sample storage as claimed in claim 11, wherein said slide plate comprises a friction reduction structure on the surface facing the inner surface of the lid element for reducing the horizontal friction between the slide plate and the inner surface of the lid element, and the transmission of the horizontal rotary force generated by the lid element to the slide plate is blocked by the friction reduction structure.

13. A sample storage as claimed in claim 11, wherein the lid element comprises a friction reduction structure on the inner surface for reducing the horizontal friction between the slide plate and the inner surface of the lid element, and the transmission of the horizontal rotary force generated by the lid element to the slide plate is blocked by the friction reduction structure.

14. A sample storage as claimed in any of claim 1, wherein the lid element can be screwed with or combined with the storage container instead of the externally equipped opaque writable element, further comprising:
   a gasket for facing directly to the top opening of said storage container;
   wherein the gasket plate comprises a friction reduction structure on the surface facing the inner surface of the lid element for reducing the horizontal friction between the gasket and the inner surface of the lid element, and the transmission of the horizontal rotary force generated by the lid element to the gasket is blocked by the friction reduction structure, only the pressing force generated by the lid element is transmitted to the gasket.

15. A sample storage as claimed in claim 14, wherein the friction reduction structure is a plurality of small prickles for reducing the contacting area to the facing surface.

* * * * *